(12) United States Patent
Hodder et al.

(10) Patent No.: US 8,644,547 B2
(45) Date of Patent: Feb. 4, 2014

(54) IMAGE ANALYSIS PLATFORM FOR IDENTIFYING ARTIFACTS IN SAMPLES AND LABORATORY CONSUMABLES

(75) Inventors: Peter Hodder, Jupiter, FL (US); Louis Daniel Scampavia, West Palm Beach, FL (US); Pierre Elliott Baillargeon, Palm Beach Gardens, FL (US)

(73) Assignee: The Scripps Research Institute, La Jolla, CA (US)

( * ) Notice: Subject to any disclaimer, the term of this patent is extended or adjusted under 35 U.S.C. 154(b) by 136 days.

(21) Appl. No.: 13/129,273

(22) PCT Filed: Nov. 16, 2009

(86) PCT No.: PCT/US2009/064565
§ 371 (c)(1),
(2), (4) Date: Jun. 23, 2011

(87) PCT Pub. No.: WO2010/057081
PCT Pub. Date: May 20, 2010

(65) Prior Publication Data
US 2011/0255745 A1      Oct. 20, 2011

Related U.S. Application Data

(60) Provisional application No. 61/114,821, filed on Nov. 14, 2008.

(51) Int. Cl.
*G06K 9/00* (2006.01)
*G01N 21/55* (2006.01)

(52) U.S. Cl.
USPC .......................................... 382/100; 356/445

(58) Field of Classification Search
USPC ............ 382/100, 191, 275; 356/51, 326, 328, 356/330, 331, 332, 33, 451, 452, 477, 138, 356/317, 318, 333, 432, 417, 445, 479; 250/316.1, 330, 338.1, 339.08, 339.11, 250/341.8; 436/171, 173
See application file for complete search history.

(56) References Cited

U.S. PATENT DOCUMENTS

| | | | |
|---|---|---|---|
| 6,734,962 B2 * | 5/2004 | Treado et al. | 356/301 |
| 7,480,035 B2 * | 1/2009 | Overbeck et al. | 356/138 |
| 7,633,627 B2 * | 12/2009 | Choma et al. | 356/479 |
| 2003/0112432 A1 | 6/2003 | Yguerabide et al. | |
| 2006/0257053 A1 | 11/2006 | Boudreau et al. | |
| 2007/0069131 A1 | 3/2007 | Banergee et al. | |
| 2007/0172855 A1 | 7/2007 | Bitner et al. | |

OTHER PUBLICATIONS

Bowes, S. et al. (2006) "Quality Assessment and Analysis of Biogen Idec Compound Library," Journal of Biomolecular Screening, 11(7): 828-835.

(Continued)

*Primary Examiner* — Abolfazl Tabatabai
(74) *Attorney, Agent, or Firm* — Duane Morris LLP; Nicholas A. Zachariades

(57) ABSTRACT

A High-resolution Image Acquisition and Processing Instrument (HIAPI) performs at least five simultaneous measurements in a noninvasive fashion, namely: (a) determining the volume of a liquid sample in well (or microtubes) containing liquid sample, (b) detection of precipitate, objects or artifacts within microliter plate wells, (c) classification of colored samples in microliter plate wells or microtubes; (dl determination of contaminant (e.g. wafer concentration}; (e) air bubbles; (f) problems with the actual plate. Remediation of contaminant is also possible.

19 Claims, 12 Drawing Sheets

(56) References Cited

OTHER PUBLICATIONS

Cheng, X. et al. (2003) "Studies on Repository Compound Stability in DMSO under Various Conditions," Journal of Biomolecular Screening, 8(3): 292-304.

Kozikowski, B.A. et al. (2003) "The Effect of Freeze/Thaw Cycles on the Stability of Compounds in DMSO," Journal of Biomolecular Screening, 8(2): 210-215.

* cited by examiner

5G.

5H.

5I.

5J.

IMAGE ANALYSIS PLATFORM FOR IDENTIFYING ARTIFACTS IN SAMPLES AND LABORATORY CONSUMABLES

CROSS-REFERENCE TO RELATED APPLICATIONS

The present application is a §371 national stage entry of International Application No. PCT/US2009/064565, filed Nov. 16, 2009, which claims the priority of U.S. provisional patent application No. 61/114,821, filed Nov. 14, 2008, which is incorporated herein by reference in its entirety.

FIELD OF THE INVENTION

Embodiments of the invention are directed to high resolution image acquisition, spectroscopy and processing instruments and methods of analyzing the quality of a sample and laboratory consumable.

BACKGROUND

The vast majority of drug and probe discovery institutions possess large ($10^5$ to $10^6$ member) compound libraries for high-throughput screening (HTS) purposes. Since the cost of a screening library compound averages between $10-100/mg, most institutions have implemented a compound management (CM) paradigm to efficiently steward this valuable asset. CM paradigms vary from institute to institute, but in general the stewardship of HTS compound libraries is shared between CM and HTS department staff.

HTS operations have benefited greatly from the availability of relatively inexpensive and standardized plastic consumables for storage of compound libraries. Currently, Polypropylene (PP) microtube racks (MTRs) and PP microtiter plates (MTPs) are the most popular consumables for storage of HTS compound libraries. Copies of compound libraries destined HTS efforts are typically distributed in a variety of formats and containers, but two paradigms currently predominate. The most popular is the "daughter plate" paradigm. In this case, a large aliquot of the compound library (approximately 10-100 microliters per compound dissolved in DMSO) is removed from the compound stocks ("mother plates") and distributed to the FITS operation in "daughter" microtiter plates (MTPs). As screeners execute multiple FITS campaigns, successive nanoliter to microliter aliquots are removed from the daughter MTP and added to HTS assay MTPs. In this scenario, a daughter plate is expected to last anywhere from several months to years. Compound libraries can also be distributed, in an "assay ready" format, where small volumes of each library compound (approximately nanoliters to microliters of compound dissolved in DMSO) are transferred directly to an HTS-compatible assay MTP; assay reagents are then added to this same plate as part of the HTS protocol, and the entire plate is discarded upon completion of the assay.

The evolution of reliable HTS automation and acceptance of HTS methodology has caused the size of institutional screening libraries to balloon. As a compound is solvated, formatted into a storage container and distributed to scientists for testing, it is subject to the introduction of artifacts. Since most institutions use similar equipment and procedures to manage and store their HTS compound libraries, a large body of relevant research has been conducted on where an artifact is introduced into compound libraries (Kozikowski et al. 2001 The effect of freeze/thaw cycles on the stability of compounds in DMSO. In 7th Annual Conference of the Society of Biomolecular Screening Baltimore; Kozikowski et al. *J Biomol Screen,* 8, 210-5, 2003; Cheng et al. *J Biomol Screen,* 8, 292-304, 2003; Bowes et al. *J Biomol Screen,* 2006). The most common artifact stems from the use of DMSO to dissolve HTS compound libraries. Although it is well known as a "universal" solvent, it is also hygroscopic. The presence of water in HTS compound libraries has a deleterious effect the solubility (and stability) of certain compounds. This source of compound precipitation (and degradation) is exacerbated by repeated freeze-thaw cycles, or by storage of compounds for extended periods of time in uncontrolled atmospheres, empty versus frill wells e.g. on a screening platform during an HTS campaign.

SUMMARY

This Summary is provided to present a summary of the invention to briefly indicate the nature and substance of the invention. It is submitted with the understanding that it will not be used to interpret or limit the scope or meaning of the claims.

The systems provided herein address an unmet need in high throughput screening (HTS) compound library management quality assurance (QA) and quality control (QC). The systems perform at least six simultaneous measurements and/or analysis of results in a noninvasive fashion, namely: (a) determining the volume of a liquid sample in wells (or microtubes) containing liquid sample, (b) detection of precipitate, objects or artifacts within microtiter plate wells, (c) classification of colored samples in microtiter plate wells or microtubes; (d) determination of water concentration (i.e. contaminant); (e) air bubbles; (f) problems with the actual plate. It also may employ methods to remediate certain artifact, such as the contaminant described in (d) above.

In a preferred embodiment, the system comprises an full spectrum, ultraviolet, visible, infrared or near infra red light source for irradiating a consumable or consumable comprising a sample; at least one lens in optical alignment with light transmitted through or reflected from the sample; at least one sensor for detecting reflected light from the sample and/or light transmitted through the sample; a computer or processor running software for processing and analyzing the reflected or transmitted light.

In another preferred embodiment, the system optionally comprises at least one filter in optical alignment with the light source and/or sensor for receiving light emitted from the light source, or transmitted through or reflected from the sample.

In another preferred embodiment, at least one sensor is in optical alignment with at least one lens for focusing light reflected from or transmitted through the consumable or consumable comprising a sample.

In another preferred embodiment, the sensor is an image sensor and captures an image of the reflected or transmitted light from the consumable or consumable comprising a sample.

In another preferred embodiment, the captured images are standardized prior to analysis by the software.

In yet another preferred embodiment, the standardization of images by the software comprises at least one step of: selecting an area of interest for analysis; compensating for environmental artifacts; comparing each pixel value to an assigned threshold value; identifying and enhancing objects; and segmenting the image. In one aspect, a Bayer filter spectral profile analysis of color space (RGB, HTS, CIE) data is conducted. Preferably, the standardized image is analyzed and results stored, in another aspect, only light within a specified bandpass is analyzed.

In another preferred embodiment, the system comprises a user interface. In a preferred embodiment, the user interface is a graphical user interface. In another embodiment, the user interface is combined with one or more databases to store, query, and retrieve relevant sample information, for example.

In another preferred embodiment, the sensor comprises a charge-coupled device (CCD), visible, UV, Near-Infra Red (NIR), or FPA NIR camera, or a single sensor capable of measuring more than one region of the light spectrum.

In another preferred embodiment, a method of detecting and analyzing artifacts in a consumable or consumable comprising a sample, comprises the steps of irradiating the sample with ultraviolet, visible, infra red or near infra red light, or a bandwidth of interest; capturing an image of light reflected from the sample or transmitted through the sample; and, processing and analyzing the image.

In another preferred embodiment, the software standardizes the image prior to analysis, said standardizing comprising at least one step of: selecting an area of interest for analysis; compensating for environmental artifacts; comparing each pixel value to an assigned threshold value; identifying and enhancing objects; and, segmenting the image.

In another preferred embodiment, analyzing comprises measuring at least one of consumable quality; sample volume, quantitative determination of DMSO and water quantities; precipitation, color classification, or contaminant remediation.

Other aspects are described infra.

DETAILED DESCRIPTION

Figure 1:
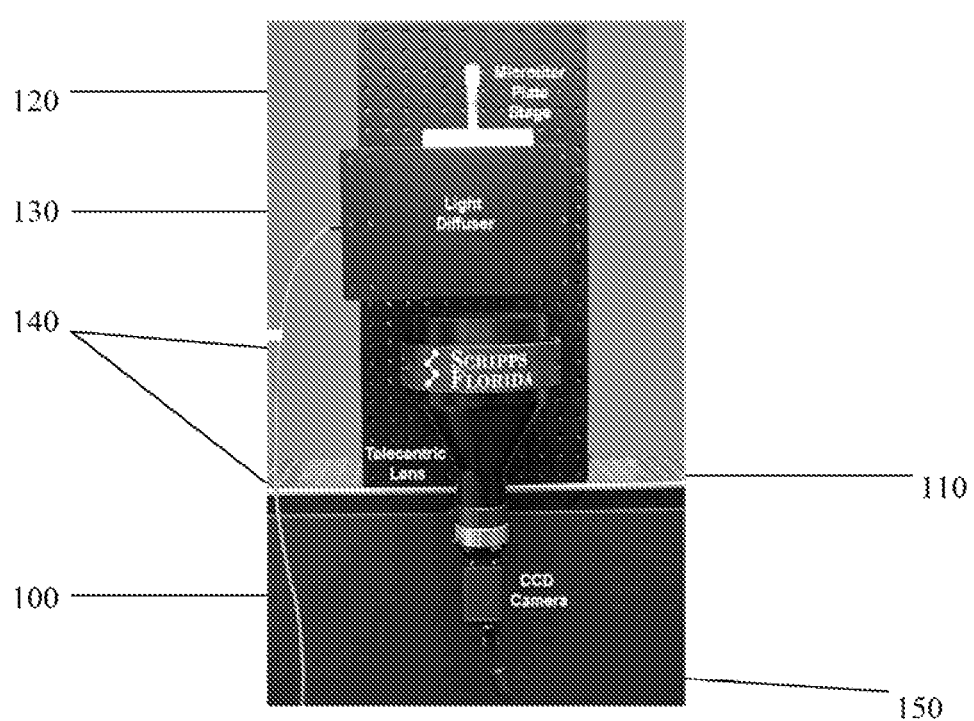
FIG. 1 is a scan of a photograph showing an embodiment of the High-Resolution Image Acquisition and Processing Instrument (HIAPI). In this embodiment, the HIAPI is configured for visible light illumination "bottom read" mode. The consumable, (e.g. microtiter plate) is placed on the stage (120), an image is captured by the graphical user interface (GUI) software which then displays the results. Analysis is completed in about minute for a 384-well plate.

High-resolution image acquisition and processing systems for detecting undesirable physical properties that may affect results in assays are provided. The system comprises one or more of: an image acquisition system; a light diffuser or emitter; sensors; filters; a consumable staging mechanism; algorithms for the processing, classifying and analysis of the information; at graphical user interface; interfacing means to a computer or computing system.

Embodiments of the systems or instruments detect undesirable physical properties ("artifact") in microtiter plates/tubes in an automated fashion. Such undesirable physical properties include, but not limited to: (1) Compound precipitate/crystallization; (2) Full, empty or partially-filled microtiter plate wells or microtubes; (3) Colored (including fluorescent) compounds; (4) Contaminant, such as water in DMSO; (5) Objects, bubbles, artifacts; (6) Quality of plate itself. Remediation of contaminant may also be desired. These systems, for example, the High-resolution Image Acquisition and Processing Instrument (HIAPI), accomplishes its analysis by innovative application of machine vision, HTS imaging and, most recently, NIR imaging and contaminant reducing technologies.

In another embodiment, a further system, termed herein, the Near-InfRared-High-resolution Image Acquisition and Processing Instrument (NIR-HIAPI), comprises a near infra red camera. This system has many advantages, including alleviating the tedious and time consuming activities associated with HTS compound library QA/QC. Both the HIAPI and NIR-HIAPI systems address these issues. Other advantages include, performing measurements in the most common consumables used by HTS and compound management (CM) labs. In one embodiment, the system, for example. HIAPI, comprises a specialized telecentric lens that images an entire microtiter plate simultaneously, such that analysis throughput is much faster (<1 minute/plate) than competitive instrumentation that employ, for example, nephelometric or acoustic detection technologies. There is no single instrument that is capable of identifying all the physical properties (artifacts) listed above. Further, the instrument is simple to use, requiring little/no calibration in routine use.

In embodiments of the invention, the HIAPI system performs five simultaneous QA measurements in a noninvasive fashion, namely: (a) quantify sample volume; (b) flag empty compound wells, (c) quantify hydration level of DMSO, (d) detect compound precipitation, and (e) classify potential assay interferants from colorimetric analysis. In addition, micro-scale remediation technology, amenable to high density (i.e. 384-wells, 1536-wells) micro-titer plate (MTP) formats, will also recover compromised compounds.

Examples of uses for the systems include, but not limited to: (i) rapid and non-destructive analysis of microtiter plates (MTP) and their compound contents. At image acquisition speeds of 125 Hz, data acquisition is rapid allowing for simultaneous assessment of all wells across a MTP. NIR complements HIAPI by providing alternative confirmation of problem wells. The NIR-HIAPI image of the MTP/tube plastic can reveal potential defects or damage to the plate itself that may hamper its proper use with HTS automation, (ii) Quantitative determination of DMSO and water quantities: unlike visible light imaging, DMSO and water are both visible and distinct in the NM range. NIR-HIAPI will quantify water absorbed and provide a spatial record of hygroscopic changes and edge-effects. (iii) Inventory solution volume: NIR absorbance is linearly dependent on path-length and hence well volume. Calibrated micro-titer plates can be quickly assessed for remaining volume of the compound solute. Since low levels of compounds (<100 mM) will not interfere, calibration by plate type is all that is needed making implementation direct and simple. (iv) QC with respect to precipitation and homogeneity: detection of compromised wells with translucent crystal precipitates can be difficult under standard visible light image analysis. However the strong CH-bond multimode vibrational absorbance in NIR is easily detected and universal for all organic compounds. The long wavelength of the NIR region (0.7-2.5 μm) creates significant light diffraction resulting in a vivid visualization of defects such as bubbles, droplets, surface tension changes and crystallization. All HIAPI instrument with NIR capabilities will analyze micro-titer plates in less than a minute providing unsurpassed throughput. HIAPI or NIR-HIAPI analysis time is independent of well density (96, 384, 1536 etc) making it forward compatible and adaptable. Unlike HPLC operational costs and materials consumed per assay is essentially nil (electricity). Other uses include, but not limited to: Chemical Imaging, 2D Fourier Transformation, Hyperspectral imaging, multispectral imaging, pixel line analyses, real-time analysis, convolution functional analysis, machine vision and the like.

In a preferred embodiment, the systems can be used at different temperatures or have the means to heat, cool, or stabilize the temperature. For example, a consumable or sample can be heated to temperatures above room temperature, or cooled below room temperatures. In one embodiment, the sample may be placed on a heating or cooling device, or the system comprises a chamber that the sample is placed in and the temperature regulated. In other embodiments the sample can be subjected to different types of atmospheres. For example, nitrogen or carbon dioxide etc., can be pumped into a chamber comprising a sample or consumable; the atmosphere can be acidic, basic etc. In one embodiment, the chamber is air tight so as to allow for controlled conditions. Oilier examples of temperatures comprise: Ambient, Room temperature, +4° C., −20° C., −80° C., Peltier. Examples of gas baths comprise Ar, $N_2$ and the like.

HTS molecular screening requires a considerable financial investment in acquiring and maintaining large and diverse chemical libraries. In compound management (CM) operations, quality standards are needed to ensure the integrity of a HTS chemical library throughout its lifecycle. To date, no universal standard has been adopted that can rapidly access compounds in a noninvasive and nondestructive fashion. Pharmaceutical libraries solvated in DMSO can degrade overtime with water absorption through storage handling processing. Moreover, screening campaigns bear additional expenses from false results due to screens that include collections of unacceptable quality, e.g. precipitates, bubbles, volumes, defects in the consumables and the like. The systems described herein, can bridge this critical need by providing rapid assessment of quality, quantity and level of hydration.

In a preferred embodiment, an innovative compound library QA/QC instrument, the High-resolution Image Acquisition and Processing Instrument (HIAPI) is shown in FIG. 1. The instrument shown in FIG. 1 is merely for illustrative purposes and is not meant to be limiting nor construed as such. Using a hi-resolution CCD camera (100) and telecentric lens combination (110), it is configured to image the top or bottom of an HTS consumable, e.g. microtiter plate or microtube receiver rack containing compounds. The consumable can be, for example, a microtiter plate comprising 96-wells, 384 wells, wells or more. Other types of consumables can be used without limitation. Once an image is captured, the HIAPI employs custom digital-image processing algorithms to identify the most common artifacts that were observed in the compound libraries, such as for example, missed (or partially filled) wells, wells where a compound has precipitated, or wells containing colored compounds. This task is performed rapidly, about 1 minute for a 384 well plate. The system or instrument is also capable of outputting the results of the analysis to a date file and archiving images to a database for future reference.

FIG. 1 is an illustrative example of the HIAPI instrument or system. In this example, the HIAPI comprises a color CCD camera (100), imaging lens (110), microplate stage (120) and brightfield illumination system (130). The hardware is mounted on an optical table (140) and connected to a high-speed laptop computer via a FireWire interface (150). Some of the distinguishing features of the HIAPI from industrial vision appliances include the combination of a telecentric lens with a high-resolution progressive scan CCD camera. The telecentric lens is capable of imagine all the wells of a standard microtiter plate or tube rack without need for repositioning the plate and with negligible perspective error; when the camera is mounted with the telecentric lens, the WAN is able to resolve features less than 1 mm in diameter with minimal vignetting and a depth of focus that is forgiving to plates that may be slightly out of ANSI-defined tolerances. In the HIAPI configuration embodiment shown in FIG. 1, illumination is provided via coaxial diffuse lighting, which is specifically suited for imaging applications where the target object is highly specular in nature. For example, microtiter plates are primarily manufactured from polypropylene, which fits into this category. The camera is communicably linked to a computer or processor. For example, the FireWire based camera was chosen to allow greater independence when choosing a software development platform, as the FireWire interface is supported by all major operating systems and image acquisition/processing/analysis software packages. However, other types of sensors and interfaces can be used, including wireless interfacing. Examples of sensors (single or array of) comprise; CCD, Photodiode, Photo multiplier tube, IR-NIR arrays, Focal Plane Array, InGaAs photodetector; VisGaAs photodetector, InSb photodetector, Quantum Well Infrared photodetector and the like.

The sensor, see, for example. FIG. 1 (CCD camera; 100) may be any device adapted for magnifying, illuminating and recording a digital image of at least a portion of the test object containing a target. This device may have a built-in magnification and illumination feature or may have an attachment that provides these features. In an embodiment, a lens-based device attachment may be used in conjunction with a standard digital camera, CCD etc., to illuminate, magnify and capture a digital image of an image. In particular, the lens-based device may illuminate and magnify an image. The lens-based device may include a housing, at least one light source for illuminating an image in a predetermined frequency range, filter(s), and a lens for magnifying the image. Similar lens-based devices, field microscopes or other illuminating and/or magnifying attachments may be fitted to virtually any form of portable or non-portable digital image capturing, device, including various types of digital cameras, scanners, cell-phones, PDAs, etc.

In general, the WAN system comprises dual-image analysis using visible and infrared camera technologies. Custom hardware compatible to future robotic integration will apply "machine vision" appliances, with optics and image analysis software. Near Infrared (NIR) imaging can provide quantitative Chemical Imaging (CI) of compound micro-plates and readily determine sample volume and hydration levels. Unlike conventional QA/QC technologies that perform sequential sample analysis, the HIAPI will perform image analyses simultaneously on the entire MTP field and will not be time limited to any appreciable extent by the format density (i.e. 96-w, 384-w, 1536-w). Most importantly, compound libraries can be subjected to rapid QA/QC prior to a HTS screening campaign to provide critical and timely validation of the data. In one embodiment, micro-scale remediation technology integrates zeolites with liquid handler micro-fluidic workstations to provide selective water removal and recovery of precipitated compounds in compromised microtiter storage plates.

Remediation means to remove a contaminant from the sample (e.g. compound & DMSO). In one embodiment, water is a contaminant of a sample and is preferably removed. For example material (e.g. zeolite, liquid chromatography material) is added to the sample well that will act as a "selective sponge." Once it is in contact with the sample, it will soak up the water that has contaminated the sample. After the water is removed by the "selective sponge", the "selective sponge" is removed from the sample. Now that the sample has no water in it, compounds that have precipitated due to water insolubility go back into the DMSO solution.

The selective sponge can be zeolite, liquid chromatography material or similar material; it can be added as a bead suspension directly to the well, or can be embedded in a pipette tip, capillary, microtiter plate lid, etc. It can be attached to an automated mandrel that dips in the well, for example an automated pipettor, etc.

Although in some embodiments, removal of water is preferred, other contaminants (e.g. unwanted chemical species such as byproducts of a organic, synthesis) can also be removed; using different materials to accomplish this.

In preferred embodiments, the systems described herein, comprise: manual, semi-automated, fully automated systems or combinations thereof.

To date, HTS compatible instrumentation is inadequate or nonexistent to qualify and maintain the vast and ever growing small molecule repositories used. Chemical Imaging and machine vision analysis is adaptable to future developments in micro-array formatting and easily integrated into existing robotic platforms or compound management systems. Success in this endeavor will produce technology that can be leveraged to government, academic screening facilities, and the biotech/pharmaceutical industry to reduce expenses and improve the quality and stewardship of HTS drug discovery libraries.

It should be understood that the programs, processes, methods and systems described, herein are not related or limited to any particular type of computer or network system (hardware or software), unless indicated otherwise. Various types of general purpose or specialized hardware and/or computer systems may be used with or perform operations in accordance with the teachings described herein.

In a preferred embodiment, light from a light source may be captured by the sensor, for example, CCD, whether the light is reflected and/or transmitted. The systems described herein can measure light that has been reflected, emitted, transmitted, refracted, polarized; also, absorbance, transmittance, phosphorescence, luminescence and the like by compound, artifact contaminant, or the consumable itself. The light can be any wavelength or can be from a light source emitting, particular wavelengths or frequency ranges. The predetermined frequency range includes ultraviolet light frequency and an infrared light frequency. The light sources may emit a concentrated portion of light on a particular area of the consumable or sample in a consumable, or may be diffused over, for example a microtiter plate. In a preferred embodiment, the system comprises a device to diffuse light, or may include a function to diffuse light placed in optical alignment with the light source. The light diffuser device may be any shape. For example, for an even distribution of light over the consumable, the light diffuser may be shaped as a "ribbed" cone. Diffuser devices may also be purchased commercially.

In another preferred embodiment, the wavelength of the light emitted by the light source may be broadened and/or narrowed by a light filter. The light filter may include a colored filter, a split field filter, a polarized filter or any other filter used in digital photography or spectroscopy. The filter can function to assist in viewing and/or capturing images. The light filter may be a long pass filter, short pass filter, or a band pass filter. A long pass filter functions to transmit a wide spectral band of long wavelength radiation thereby blocking short wavelength radiation. A short pass filter functions to transmit a wide spectral band of short wavelength radiation thereby blocking, long, wavelength radiation. Examples of filters comprise without limitation, one or more of: Polarized, Atttenuated, dichroic, emission, excitation, Longpass, Shortpass, Bandpass, Notch Coated, Dielectric, light, diffuser.

The type of light source can be varied, in many cases, the light source may be an LED, incandescent bulb, fluorescent bulb, or halogen bulb. LEDs have advantages because they are typically of small size, but still produce a substantial amount of light versus the amount of power they consume. The light source may provide constant illumination or a momentary flash timed to coincide with image acquisition. The flash device or other light source may include a filter to tailor the illumination spectrum. Power can be delivered, to the light source by any electrical power source, including battery power is preferred to make the lens-based device mobile and independent of its proximity to a stationary power supply, such as an electrical outlet.

In another preferred embodiment, a light source comprises a single light source, an array of light sources comprising the same light source or a combination of different light sources. Examples include, without limitation: blackbody radiator, IR, UV, visible, laser, monochromatic, polychromatic, LED, tungsten-halogen, quartz-tungsten halogen. Hg arc lamp, Xe arc lamp, or Electroluminescence.

In one embodiment, light is provided by one or more laser sources, and/or an illumination lamp, such as, for example, a xenon (Xe) lamp, or a mercury (Hg) lamp optimized for broadband illumination. Examples of lasers include, but not limited to a solid state laser providing. UV/violet light, such as, for example, a gallium nitride laser diode operating at wavelengths in the range of 380 nm to 420 nm; a solid state laser operating in the red, such as, for example, a diode laser operating at wavelengths in the range from of 630 nm to 670 nm, such as, for example, an AlGaInP laser diode.

In another embodiment, the light source comprises a laser diode operating in the red (e.g., from about 630-670 nm) a laser diode operating in the green (e.g. from about 500-550 nm), and a laser diode operating in the violet (e.g. from about 380-460 nm). In one version, the red, green and violet laser diodes are operated to provide both "white light" to serve as an illumination light source and excitation light. For example, corrected broadband illumination ("white light") can be provided by controlling the intensity and bandwidth of the light that reaches the tissue front each the three laser diodes. Excitation light could, e.g., then be provided by the violet laser diode, by frequency doubling the light from the red laser diode (e.g., with a $KTiOPO_4$(KTP) crystal), or both, to provide one or more excitation wavelengths.

In one embodiment, the system comprises an optical table upon which the consumable is placed. Although, neither the consumable nor the camera is required to move in order to provide the analysis of the consumable or sample in a consumable, the camera may be mounted such as to allow movement of the camera. In other preferred embodiments, the light source, filters, diffusers etc., can be stationary or have the ability to move in any directions or angles, depending on how the user would desire the system to be configured. Examples of different configurations of the system comprise: stage movable, lens and/or sensor fixed; stage fixed, lens &/or sensor movable, lens fixed, sensor &/or stage movable; epi-illumination imaging, trans-illumination imaging, split-beam dual detector systems, diffuse axial illumination imaging, directional illumination imaging, glance illumination imaging, diffuse illumination imaging, darkfield illumination imaging, backlighting illumination imaging or any combinations thereof.

The components of the system may be interconnected via any suitable means including over a network, e.g. the HIAPI to the processor or computing device. The processor may take the form of a portable processing device that may be carried by an individual user e.g. lap top, and data can be transmitted to or received from any device, such as for example, server, laptop, desktop, PDA, cell phone capable of receiving data, BLACKBERRY™, and the like. In some embodiments of the invention, the system and the processor may be integrated into a single unit. In another example, a wireless device can be used to receive an image and forward it to another processor over a telecommunications network, for example, a text or multi-media message.

The functions of the processor need not be carried out on a single processing device. They may, instead be distributed among a plurality of processors, which may be interconnected over a network. Further, the information can be encoded using encryption methods, e.g. SSL, prior to transmitting over a network or remote user. The information required for decoding the captured encoded images taken from test objects may be stored in databases that are accessible to various users over the same or a different network.

In some embodiments, the data is saved to a data storage device and can be accessed through a web site. Authorized users can log onto the web site, upload scanned images, and immediately receive results on their browser. Results can also be stored in a database for future, reviews.

In some embodiments, a web-based service may be implemented using standards for interface and data representation, such as SOAP and XML, to enable third parties to connect their information services and software to the data. This approach would enable seamless data request/response flow among diverse platforms and software applications.

In another preferred embodiment, the system comprises a plurality or array of sensors. Each sensor may differ, for example, a CCD camera and a NIR camera. See, for example, FIG. 11. Other examples of sensors comprise CCD, Photodiode, Photo multiplier tube, IR-NIR arrays, Focal Plane Array, InGaAs photodetector, VisGaAs photodetector, InSb photodetector, Quantum Well infrared photodetector or combinations thereof. In general, the detector system comprises a charge coupled device (CCD), a CMOS imaging device or other pixelated imaging sensor. In addition, in preferred embodiments of the systems of the present invention, the detector system includes a frame grabber to acquire images, e.g., of the consumable under investigation. Preferably, images are acquired for every reference location in a consumable and consumable comprising a sample from which spectra are obtained.

In another preferred embodiment, the image may optionally be magnified by the image acquisition device or a lens-based device used in conjunction with the image acquisition device. The image acquisition device may include a magnifying lens with magnification capability or an attachment having lens with magnification capability. The magnifying lens may magnify the image for viewing and/or capturing. The magnifying lens may allow an image to be viewed and/or captured from about 0.01 microns to 10 microns. In some embodiments, the lens may be a 10-60× lens. The lens in lens may be interchangeable and may interact with a zoom lens or regular lens of the image acquisition device. The lens ma interact with the flash of an image acquisition device. Further, the lens may interact with the image acquisition device to increase or decrease the magnification of the image. The magnification of the lens may be manual or automatic. Additionally, the lens may be a physical lens or an electronic/digital lens. Other examples of lens comprise Telecentric, Achromatic, Wide angle, High F-number, Low F-number, Zoom, Quartz. Borosilicate, glass, plastic, sapphire; imaging fiber-optics or combinations thereof.

In a preferred embodiment, a magnified digital image of the test object is captured using the image acquisition device (100). The captured digital image may include all or a portion of the object. The captured digital image may be configured so that only the target area (Area of Creation) is captured or may be configured so that the target area is included in a larger view. In either case, the captured image may also include identifiable orientation marks that allow the identification and proper orientation of the target area portion of the captured digital image. The captured digital image may be downloaded to or sent to a processor. At the graphical user interface (see, for example, FIG. 2) the captured digital image is viewed and or processed by the processor. Some or all of the processor may be co-located with the inspection site (i.e., the location where the digital image of the test object is captured) and some or all of the processor may be remote from the inspection site. In either case, the processor may be connected to the image acquisition system over a network. The captured digital image may be transmitted over the network in any manner such as by e-mail or other transfer process. In some embodiments, the digital image may be transmitted over a wireless telephone or other telecommunications network. It can also be sent as an attachment to any form of e-mail or text or multi-media message.

Figure 2:
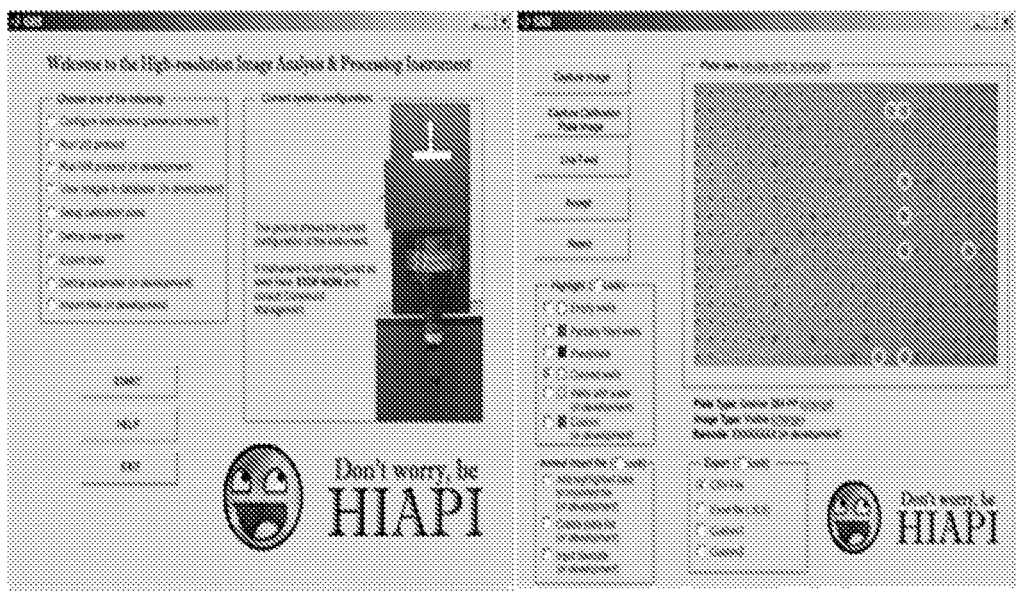
FIG. 2 is a scan of a photograph showing a page of the graphical user interface (GUI). Through the selection of one of the radio buttons, the different functionalities of the HIAPI can be accessed.

In another preferred embodiment, the system comprises a user interface. In a preferred embodiment, the user interface is a graphical user interface. Referring to FIG. 2 which represents one embodiment of the graphical user interface (GUI), was written in MATLAB®, MATLAB® is a high-level technical computing language and interactive environment for algorithm development, data visualization, data analysis, and numeric computation. However, any computing programming language can be used in designing and implementing in the graphical user interface.

A variety of software packages which are commercially available can be employed in embodiments of the invention. For example, National Instruments Vision Builder (NIVB) and MATLAB® for HIAPI's image analysis applications. Both these software packages provide a library of common image processing and analysis toolboxes; these tools allow development to focus on implementation of novel solutions by pulling from a library of well proven algorithms and functions. Other examples of software packages include: Deblurring, Enhancement, image Arithmetic. Image Registration, Image Segmentation, Spatial Transformation, Measuring Image Features and Transforms processing algorithms. In MATLAB®, these algorithms are accessed by calling them as functions with various parameters, such as an image frame, passed through to the function, HIAPI commands may be issued in a command window for immediate processing or written with other commands into MATLAB® M-tiles which can be later executed. NIVB provides functionality similar to that which is available in MATLAB®, however NTVB allows users to construct imaging applications through a graphical user interface (GUI). This allows the user to drag and drop components into a workspace, connect them as needed and set parameters without having to write any code.

In some embodiments, the data processor may implement an analysis program and/or functionality of the methods of the present invention as software on a general purpose computer. In addition, such a program may set aside portions of a computer's random access memory to provide control logic that affects the analysis program, light source control, detector systems spectra acquisition, and the operations with and on the measured images. In such an embodiment, the program may be written in any one of a number of high-level languages, such as FORTRAN, PASCAL, C. C++, or BASIC. Further, the program may be written in a script, macro, or functionality embedded in commercially available software, such as EXCEL or VISUAL BASIC. Additionally, the software could be implemented in an assembly language directed to a microprocessor resident on a computer. For example, the software could be implemented in Intel 80×86 assembly language if it were configured to run on an IBM PC or PC clone. The software or code may be embedded on an article of manufacture including, but not limited to, computer usable medium such as a hard drive device, a CD-ROM, a DVD-ROM, or a computer diskette, programmable logic controller, BASIC-STAMP, microchip, etc. having computer readable program code segments stored thereon.

It will be apparent to those of ordinary skill in the art that methods involved in the system and method for light scattering spectroscopy may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

The processor may be configured to automatically carry out some or all of the remaining steps of the method as described in detail in the examples section which follows. If necessary, the software or algorithms may compare the object or consumable, via the captured image frames or images, with certain predetermined criteria or controls, which may include an expected control. Also, if the image is an encoded image, the processor may decode the image. In such instances, the processor may determine one or more of the encoding parameters used to encode the image. The number of parameters required may depend on the specific digital decoding methodology used. The encoding parameters may be obtained from data storage where they are placed at the time of encoding. This data storage may be a part of or co-located with the processor or may be disposed in a separate database processor or server accessible to the processor over a network. The data storage may also take the form of a magnetic stripe, laser card, smart, card, processor chip, memory chip, flash memory, sample ID or bar code, which can be applied or attached to or otherwise associated with an object to which art image is applied. The encoding parameters may be object-specific or may be constant for a particular set of objects. In some embodiments, some or all of the encoding parameters may be received with an encoding request or determined from the content of the image.

In some embodiments, the method may be adapted to determine whether the captured image or certain captured frames comprise micro-printing or rasters formed as a particular shape. Such printing devices may be identified in both encoded and non-encoded images.

The processor may use object landmarks to orient the target area of the captured digital image for viewing and/or decoding. These landmarks may be based on the inherent geometry or topology of the object or may be specifically applied. The presence of such landmarks could be used as an initial check. It will be understood by those of ordinary skill in the art that if the digital image is captured in such a way that the object is always oriented in exactly the same way relative to the image acquisition device, there may be no need for digital orientation of the captured image. For example, if the test objects are documents that can be precisely positioned for scanning, the orientation of the target area may be sufficiently constant that orientation of the captured digital image is unnecessary.

If a comparison is desired, this may involve a sequence of criteria beginning with whether an image is even present in the target area. If an image is present, it may be directly compared to a control image or compared to any number of images which may have been stored or are being captured as part of the quality control and quality assurance, for example, variation parameters within a set of consumables or manufactured lots of consumables or consumables comprising a sample, can be determined. Thus, if there is a large variation between lots or within a lot then these may be eliminated from being sent to a user. The samples and consumables can be further processed to provide a result that can be compared to a control image or information derivable from control or images from a manufactured designated lot. Thus, verifying the quality of the consumables may comprise, inter alia, the actions of viewing the captured image an/or comparing it to an expected image, decoding the image, and deriving information from the captured image or a decoded version of the captured image.

Optical magnification may be used in conjunction with the digital decoding method to reduce the influence of imperfections in the captured digital image and improve the ability to sample the captured digital image. In some embodiments, the methodology samples one or more lines of the captured digital image at certain desired frequencies and angles. For example, one or more sampled lines of the captured digital image may be combined to generate one line of a result. The optical magnification of the image can determine the actual pixel spacing between the sampled lines. The physical spacing of the image should match the lines spacing used during the analysis of the control, or the line spacing of the equivalent magnifying lens. The number of pixels between the sampled lines of the magnifying lens is calculated. A physical measurement, such as picture of a calibration grid, may be used to obtain a scale factor for the magnifying, lens. The physical measurement may be calculated automatically. The methodology enhances the sampled lines of the captured digital image to remove any gaps between lines to produce a result.

Although not necessary with the systems of the invention and embodiments thereof, when viewing and/or capturing an image one may also consider determining the actual pixel-per-inch resolution of the captured image; and compensate for the different types of geometrical distortion that can be induced by the image acquisition device. Assuming the image acquisition device maintains the same distance from the object and the zoom function is not used. For example, the image acquisition device is positioned directly on the surface of the object thereby providing a consistent capturing distance. However, if the zoom function is used or the image acquisition device does not maintain a consistent distance, pre-calculated values are difficult to use. The positions and distances of the reference points on the object and the scale factors of the image will need to be recalculated, for example, when a new type of consumable or sample is to be analyzed.

Numerous methods may be used to determine the actual pixel-per-inch resolution of the captured image. The preferred methods are described in detail in the examples which follow. Two of the methods are using calibration to determine the real pixel-to-pixel resolution of the image and rescaling a frequency.

The digital camera can be calibrated to determine the real pixels-per-inch resolution of the viewed and/or captured image. The scale factor of the digital camera can be calculated. The scale factor calculation occurs by taking a picture of a reference pattern, whose physical dimensions are known. Alternatively or in addition, the image acquisition device or attached lens device may produce repeatable effects on captured images that may be used as a reference. For example, a magnifier may limit the captured field to a circle with a known, fixed diameter. In either case, if there are 1800 pixels covering one inch of the reference pattern then the resolution is 1800 pixels-per-inch. Next, the scale factor can be determined by dividing the reference pattern resolution by the actual resolution.

Geometrical distortion may also be considered when viewing and/or capturing an encoded image. Misalignment and/or rotation can distort an object, however, both can be compensated by decoding software. The decoding software can calculate the angle of rotation in the viewed and/or captured image. Of the many methods used to calculated the rotation angle one can use the positions of some easily located reference points on the object or looking for a maximum of a Radon transform for an image with dominant line structures. Once the rotation angle is calculated, the captured image may be held in its referent position, to avoid distortion caused by the rotation process (e.g. interpolation on the digital grid blurs the image). The encoded image decoding parameters use the adjusted rotation angle. For example, if an encoded image is embedded with 15 degrees screen angle, and it can be calculated that the object in the captured image was rotated by 3 degrees the adjusted angle of 15+3=18 degrees should be used for the decoding algorithm.

Figure 3:
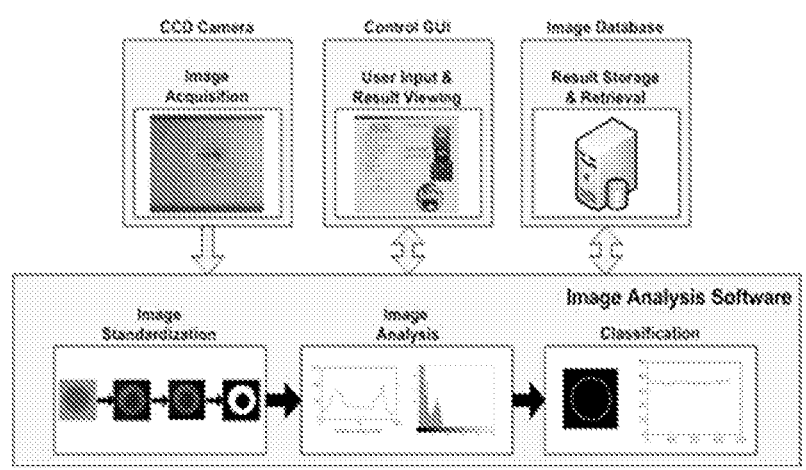
FIG. 3 is a schematic illustration of HIAPI image acquisition, standardization and analysis process. Once an image is captured by the HIAPI's optical subsystem, the image is passed to the HIAPI's computer memory for processing and analysis. Data retrieval for offline analysis is also illustrated.

After turning on the instrument and launching the HIAPI software, a "start page" GUI interface is displayed (FIG. 2, right panel). After verifying that the picture on the screen coincides with how the hardware is actually set up, the first decision the user makes is whether instrument calibration is necessary. Calibration is unnecessary if the HIAPI has already been calibrated with the particular brand of microtiter plate consumable the user wishes to analyze. If calibration is desired, the user prepares and measures calibration plates (e.g. an empty plate, a plate, filled with DMSO or other appropriate controls) on the HIAPI and performs a prescribed calibration routine. This normally takes 10-15 minutes. Once instrument calibration is completed, the user selects the appropriate protocol to run from the GUI, and the image acquisition/results display window appears (FIG. 2 right panel). The user then places the test microtiter plate/tube receiver rack on the imaging stage, selects what artifacts he is interested having the HIAPI classify, and starts the HIAPI measurement protocol. Since all of the systems can be fully automated, a consumable can be placed by mechanical means, such as for example, a robotic arm, moving, belt or other automated mechanical means, and the appropriate software protocol can be selected via software interface. As the user waits for the HIAPI to finish its measurement protocol, the following processes are executed by the HIAPI. FIG. 3 is an illustrative example of a general scheme of such process. In an embodiment of the process, the steps can be broken down into different steps: (i) image acquisition which involves the use of an imaging acquiring device, such as for example, a camera; (ii) image standardization which comprises a graphical user interface or software automation; (iii) image analysis and classification which comprises processing an image matrix through algorithms wherein image descriptors are calculated and used for classifying the information obtained from the image; (iv) completion and storage which comprises aggregating, formatting, the data and display of the data by the graphical user interface or other appropriate means.

(i) HIAPI Image Acquisition.

In one embodiment, immediately after the measurement protocol is initiated, the HIAPI software captures a frame from the CCD camera and imports this frame into the HIAPI computer's RAM memory. At this point in the process, the microtiter plate/tube receiver rack image is digitized as a 3-dimensional matrix. This 3-D matrix can be thought of as three stacked two-dimensional matrices, where each 2-D matrix (X- and Y-axes) represents the 2-D image (length and width) of each color imaged by the CCD (i.e. red, green or blue) and the Z-axis contains the values of the three color channels associated with the image. Other colors determinations comprises use of filters like, for example, bandpass filters, Bayer filters, absorptive filters, dichroic filters, infrared filters, ultraviolet filters, neutral density filters, lone filters, shortpass filters, guided-mode resonance filters, polarizers, and the like.

(ii) HIAPI Image Standardization.

After acquisition, HIAPI digital image processing tools subject the captured image to a series of filters that standardize its features before analytical processing begins. This standardization process can consist of the following steps: (1) Area of Interest (AOI) Creation: In this step, sections of microtiter plate (e.g., the border and skin of the plate) are not needed for further analyses are discarded. Since the compound plate/tube receiver rack being interrogated is located in a rigid plate stage, the AOI is determined only once (during instrument calibration) for each plate type and then fixed within every image that HIAPI captures thereafter from that particular plate type. Any information outside the AOI is discarded in this step, as it provides no useful information and increases the amount of time required for downstream image processing. In the case of the 3D matrix, this is accomplished by discarding a fixed border in each of the color channels. (2) Application of environmental corrections: Any compensation needed to correct for artifacts due to illumination conditions, optical distortion by compound plate features, etc. is corrected in this step. One method the HIAPI uses to correct for environmental conditions is to perform "image subtraction." In this procedure values from the calibration image matrix (as with the AOI, stored during instrument calibration) are subtracted from the current image matrix. A simple example of this type of correction would be if dust or particulate were to settle on the telecentric lens of the HIAPI. Detected during calibration, it would be subtracted from each image the HIAPI acquired to ensure it was not categorized as a false-positive. (3) Threshold Determination: This is actually a two step procedure where the RGB image is converted to grayscale and then further into a single, 24) binary image. The conversion from grayscale to binary compares each pixel value against a given threshold to determine if the value of that pixel should be ultimately represented as a 1 or 0. In some cases, the HIAPI can use a histogram approach, known as Otsu's method (Otsu *IEEE Trans. Sys., Man., Cyber*, 9: 62-66, 1979), to determine threshold. (4) Object Identification and Enhancement: The HIAPI can use built-in library functions to enhance and identify objects, such as morphological operators. These morphological operators are capable of enhancing and identifying objects then determining their relevant properties. The result of all morphological, operations is an image frame where all objects have been outlined, filled in and dilated to make final analysis possible on an image where contrast between distinct objects has been maximized. In addition to morphological operations, objects are further identified and classified by means of histograms and intensity profiles. The data provided by these histograms and intensity profiles can represent unique 'thumbprints' which provide information about the shape, color and intensity of items in the wells/tubes of the microtiter plate/microtube rack. (5) Image Segmentation: The last step of image standardization the HIAPI can perform is a virtual segmentation of the image to separate the plate/rack into individual wells/tubes for analysis. In other words, the 2D binary image matrix is partitioned into a series of much smaller 2D matrices, with each smaller 2D matrix representing a single well/tube of the plate/rack.

(iii) HIAPI Image Analysis and Classification.

Following image standardization, the data for each 2D binary image matrix can be processed through algorithms in the HIAPI software which calculate image descriptors and use these descriptors to classify the resulting information. This includes (but is not limited to) calculating boundaries of objects within the image frame and then plotting the distance versus angle signatures of these boundaries. Signature and boundary information is then analyzed in concert with histograms, image profiles and properties extracted through morphological operators in previous steps to classify the contents of the well. The results of each well's classification are recorded into memory and the process is repeated until all wells have been analyzed.

(IV) HIAPI Performs Image Capture and Analysts Rapidly.

For one microtiter 384-well plate, the time is about 1 minute. Further, the amount of time, required to image and analyze a plate is independent of plate density due to the nature of the system. Specifically, a plate containing 384 wells has roughly the same number of pixels containing well information as a 1536 well plate. This is because while the number of wells has increased by a factor of four, the number of pixels representing each well has decreased by a factor of four.

(v) Completion of the HIAPI Measurement Protocol.

Once analysis is completed, classification data for the entire microtiter plate (or for each well measured) can be aggregated and formatted into a report for the user to view through the HIAPI's GUI interface. At this point, the user is prompted as to whether to discard the image or save the image and the corresponding analysis. The user may also edit parameters for custom applications. IF the image and results are saved, the original source image, along with frames from any of the preceding steps is stored in the HIAPI's database. A full-color image and a *.csv file are also saved on the HIAPI computer hard drive, which is readily accessible to the user if desired.

Image Acquisition, Standardization; Color "Artifact" Determination, Empty-Well "Artifact" Determination.

Figure 4:
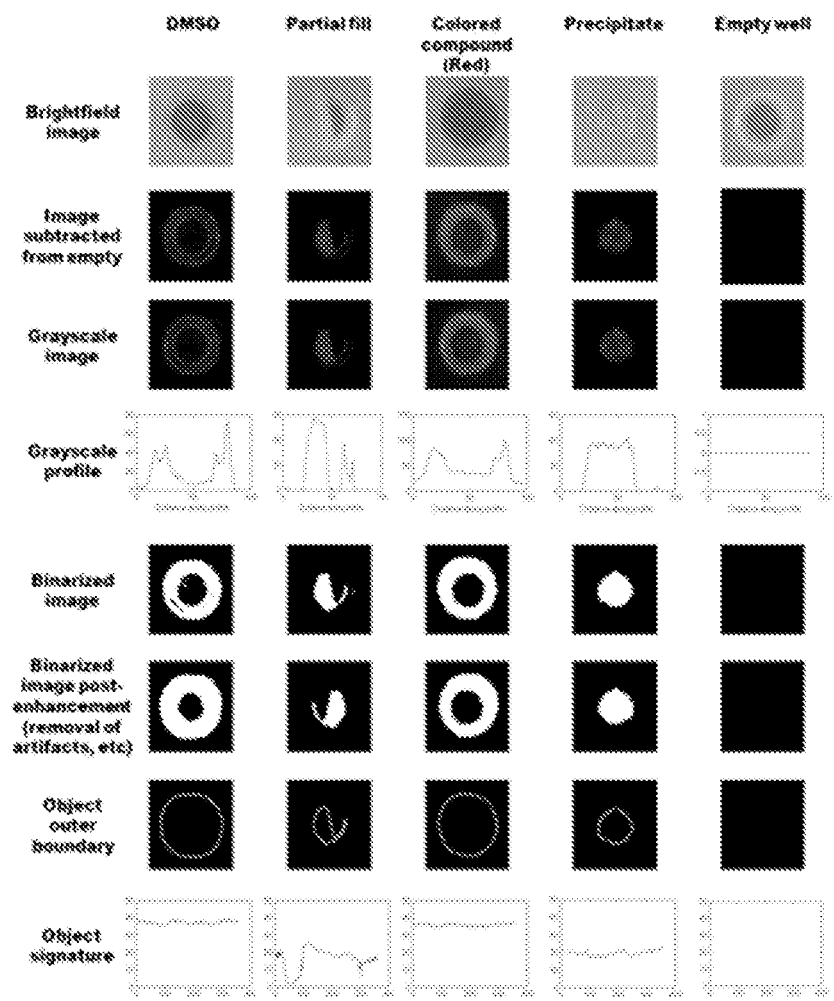
FIG. 4 shows examples of MTP well types from a Greiner 384-w polypropylene plate. (Left to Right) A normal DMSO filled well, partial filled well, colored compound, precipitated compound, and an empty well are analyzed using the MATLAB software applications.

The HIAPI software processes begin when all image data is imported from the CCD camera into HIAPI's computer memory. FIG. 4 illustrates how the HIAPI is capable of enhancing the images of microtiter plate wells/microtube receiver rack into meaningful quantitative information that enables automated classification. After selection of the AOI, one of the first steps in the HIAPI performs is the extraction of color information, which is analyzed in terms of pixel intensity at each color channel. Clearly visible in the first row of "raw" CCD images in FIG. 4 is the presence of a red compound. The resulting histograms from this image are immediately used to determine the color(s) present in a well ("red"); the amount of variance in color across a well is also important, since it combined with other downstream determinations (i.e. "precipitate") to better classify the type of artifact present in the well ("red"+"precipitate"="red precipitate"). Following the extraction of all color channel histogram data, image subtraction is performed as a method of environmental correction; i.e. HIAPI compares the interrogated well to an empty well or deduces that the well is empty based on pre-determined parameters. If a well is empty, it results in a "black" image and there is no further processing necessary. If the well is not empty, then the resulting image highlights the distinguishing features quantified in its 2-D matrix.

The next step, illustrated by FIG. 4, is the conversion of the image subtraction result into grayscale. This removes color information, which is necessary for downstream processing. While this is a 'flattening' of the image from 3-D to 2-D, the intensity values representing objects of interest are retained. When the image is at this stage, meaningful information can be obtained in the form of grayscale histograms and "distance" profiles (FIG. 4). Grayscale histograms and distance profiles provide an assessment of pixel intensity across a selected cross-section of the well. In the case of the HIAPI analysis illustrated in FIG. 4, the selected cross-section passes horizontally through the center of the well. The last stage of image processing uses a threshold to convert the grayscale image to a binary image. The end result represents the objects present in a given well that had an intensity greater than the defined threshold. These binary objects undergo enhancement routines to remove spurious objects which might otherwise be identified as false positives in downstream analyses. Finally, the enhanced binary objects can be put through algorithms to extract and plot their boundaries, known as "signatures" (FIG. 4).

Image Analysis; Precipitate, Partially Filled Well Determination & Classification.

With all of the information from the preceding steps, final image analysis combines object signatures, morphological properties, histograms and distance profile information together to determine how the contents of a well should be classified. From FIG. 4, it can be seen that certain patterns exist; these and the results of other algorithms) can be distinguished from each other as follows: 1) Partially filled wells have object signatures which are erratic in shape and have significant variation in amplitude across the signature. In terms of morphological properties, the centroid location will be offset from the center of the image and object area will be noticeably less than the area of the well which is pre-determined during the calibration of the HIAPI. 2) "Normal" wells (those containing enough compound liquid to cover the bottom of the well and without precipitate), have binarized objects which look similar to toroids ("donuts"). The signature for these objects is flat; the centroid of the object analyzed is very close to the absolute center of the image and its area is equivalent to the area of the well. Calculation of an Euler number also aids in the analysis of these images; in this case it represents the number of objects detected in the image, minus the number of holes in the objects. "Normal" wells have an Euler number of about 0.3. Empty wells will be represented by a black image frame after image subtraction in all cases, so no further properties are necessary for classification. Wells containing, precipitate are represented by a solid circular object in the binarized image and have flat signatures, similar to non-problematic wells. However the amplitude of the signatures is significantly lower than seen in the signature of a non-problematic well. These wells typically also have an Euler number of 1, an object area equivalent to half the area of the well and a centroid located in the center of the well.

The HIAPI is fully capable of automated artifact analysis in a variety of HTS consumables. See, the Examples section which follows and Table 1.

In a preferred embodiment, one or more filters are employed in the HIAPI and NIR-HIAPI systems. For example, use of optical filters (e.g., cold filters) that block the visible wavelengths (0.4-0.78 μm), charge-coupled devices (CCDs) used in digital cameras and camcorders can be used to sense NIR light out to around 1100 nm. Other regions of the NIR spectrum can be viewed using devices such as indium gallium arsenide (InGaAs—0.9 μm to 1.7 μm) and indium antimonide (InSb—1.0 μm to 5.0 μm) focal plane array (FPA) detectors. These integrated wavelength NIR imaging approaches allow one to study relative light intensities of objects over broad ranges of the NIR spectrum.

In another preferred embodiment, the filters comprise one or more of: Polarized, Attenuated, dichroic, emission, excitation, Longpass, Shortpass, Band pass, Notch Coated, Dielectric, light diffuser, polarizing or combinations thereof.

The use of dielectric interference filters in combination with NIR FPAs is one method in which chemical information can be obtained from a sample. To form NIR chemical images, a NIR light beam is defocused to illuminate a wide field of view and the reflected or transmitted light from the illuminated area is imaged onto a two-dimensional NIR detector. A selection of discrete dielectric interference filters provided in a filter wheel, or a linearly variable or circularly variable format can be positioned in front of a broadband NIR light source, or in front of the NIR FPA itself in order to collect NIR wavelength resolved images. Typically, the use of several fixed bandpass filters is sometimes needed to access the entire NIR spectrum. The spatial resolution of the NIR image approaches that of the optical microscope, while spectral resolution of several nanometers has been demonstrated.

Acousto-optic tunable filters (AOTFs) have been employed as no-moving-parts imaging spectrometers for NIR imaging. The AOTF is a solid-state device that is capable of functioning from the UV to the mid-IR depending on the choice of the filter's crystal material. Operation of the AOTF is based on the interaction of light with a traveling acoustic sound wave in an anisotropic crystal medium. The incident light is diffracted with a narrow spectral bandpass when an RF signal is applied to the device. By changing the applied RF frequency under computer control the spectral passband can be tuned rapidly with the benefit of non-moving parts.

In another preferred embodiment, imaging can combine diffraction-limited spatial resolution with high spectral resolution allowing for collection of high resolution (spectral and spatial) data using liquid crystal (LC) imaging spectrometers. In general, LC devices provide diffraction-limited spatial resolution. The spectral resolution of the LC imaging spectrometer is comparable to that provided by dispersive monochromator and Fourier transform interferometers. In addition, LC technology provides high out of band rejection, broad free spectral range, moderate transmittance, high overall etendue and highly reproducible random access computer controlled tuning.

Under normal NIR imaging operation, LC imaging spectrometers allow NIR chemical images of samples to be recorded at discrete wavelengths (energies). A spectrum is generated corresponding, to thousands of spatial locations at the sample surface by tuning the LC imaging spectrometer over a range of wavelengths and collecting NIR images systematically. Contrast is generated in the images based on the relative amounts of NIR absorption, transmittance or reflectance that is generated by the different species located throughout the sample. Since a high quality NIR spectrum is generated for each pixel location, a wide variety of chemometric analysis tools, both univariate and multivariate, can be applied to the NIR image data to extract pertinent information. Correlative multivariate routines are particularly powerful when applied to chemical images collected from samples intentionally seeded with a known standard material. This approach of incorporating calibration standards within an image field of view can be extended to quantitative chemical image analysis. In addition, digital image analysis procedures can also be applied to high image quality NIR chemical images to perform routine particle analysis in both two (2D) and three (3D) spatial dimensions. Volumetric 3D NIR chemical image analysis can be performed very effectively using numerical deconvolution computational strategies.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Figure 10:
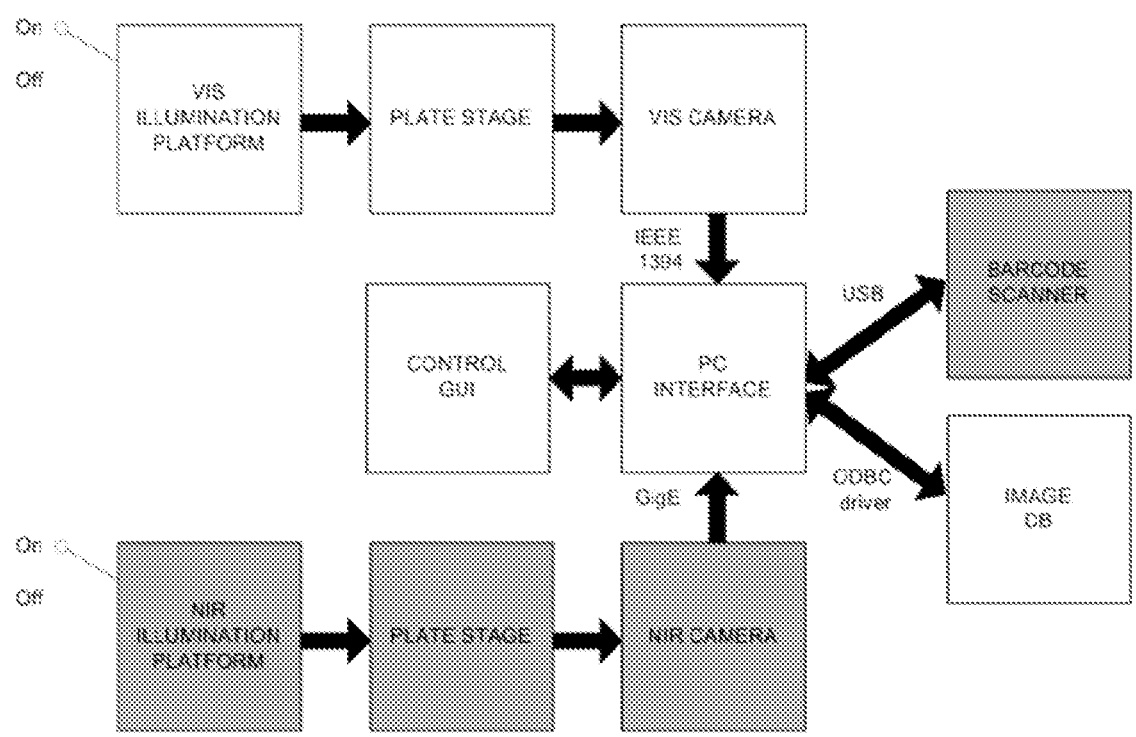
FIG. 10 is a schematic illustration showing an embodiment of the High-resolution Image Acquisition and Processing Instrument (HIAPI) configuration scheme. The white boxes represent subsystems that are used for visible light applications on the HIAPI, the boxes represent added functionality for NIR applications and barcode scanning.

NIR-HIAPI Instrument Fabrication:

NIR imaging in a transmission-mode requires that the near-infrared light source be placed to penetrate through a MTP for measurement by a NIR detector on the opposite side. Transmission mode measurements provide an average signal from the depth (z-axis) while maintaining spatial separation across the pixel plane (x, y axis). Due to the nature of NIR and its weak absorbance interactions, transmittance mode measurements are well suited to ascertain solvent (e.g. DMSO) and contaminant (e.g. water) content. Several key pieces of hardware can be incorporated into a HIAPI platform (FIG. 10).

Figure 11:
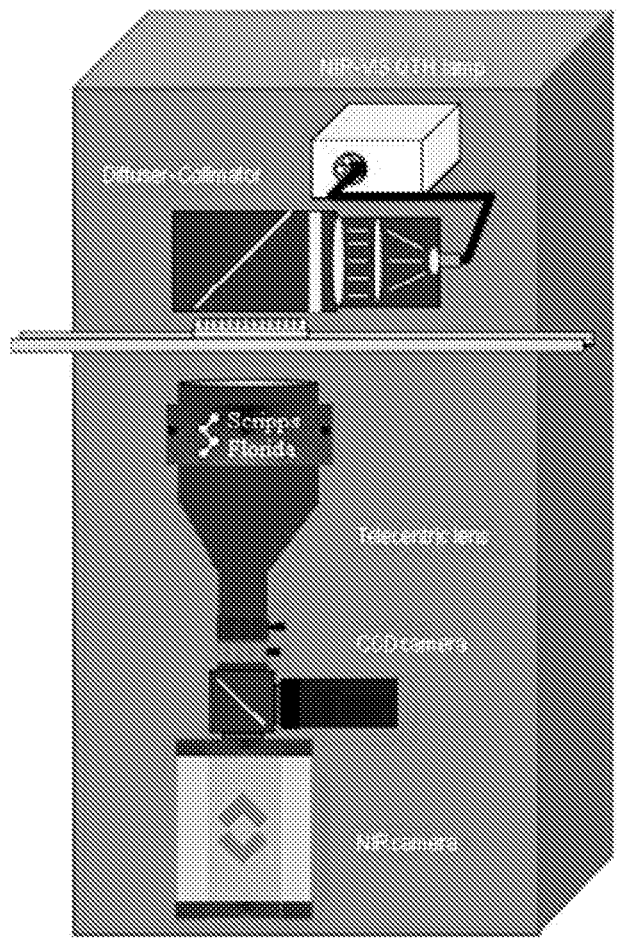
FIG. 11 is a schematic illustration showing an embodiment of the NIR-HIAPI configuration scheme. This embodiment shows a configuration in a bottom-read mode. Other embodiments include combination of the sensors, such as, for example combining vis, NIR.

Camera Integration:

State of the art NIR cameras use InGaAs focal plane arrays (FPA) with outstanding sensitivity in the 900-1700-µm range. Unlike earlier NIR cameras, no special cryogenic support hardware was needed, simplifying integration and support. Data acquired using a 320×256 FPA provided adequate resolution for prototyping and testing. High performance NIR cameras are currently available using 640×512 FPA which increase pixel resolution by 4-fold, desirable for full plate imaging. Newer NIR cameras are capable of a programmable frame rate of 1-125 Hz, 14 bit dynamic range and a 50 MHz data transfer rate allowing for rapid image acquisition and minimal MTP exposure to the environment and infrared heat. Cameras with combined visible light and NIR sensitivity are also available. The FPA sensors are of the ⅔" or 1" array types requiring a lamer lens mount (45 min or F-mount) than the smaller CCD VIS detectors (C-mount). See, for example. FIG. 11 for optimal placement of the two cameras in a prototype.

NIR Camera/Telecentric Lens:

NIR light in the 0.7-1.7 micron range is highly compatible with most standard glass optical components used for visible light imaging. Optical lens/filters made of plastics should be avoided to minimize NIR loss. Telecentric lenses also require customized optical coatings to correct for chromatic aberration and focal plane when using NIR light. However said, the corrections needed produced an acceptable VIS image when properly coupled to a higher resolution (5 to 8-MP) CCD used camera. A customized NIR telecentric lens was obtained to evaluate NIR and VIS camera performance. A single optical train with image splitter can also be pursued. In another alternative, the HIAPI can have two separate optical trains for dual camera integration into a single instrumental platform. Another option is to select a NM camera with an extended VIS scan range of 0.4-1.7 microns, with RGB filters on the filter wheel to extract colorimetric in formation.

QTH NIR Light Source/Diffuser:

NIR as well as VIS light is efficiently generated by most blackbody sources including quartz tungsten halogen lamps. DC-regulated fiber optic illuminators with low output power ripple (<0.4%) are readily available for machine vision lighting. Variable intensity control and filter mounts may also required to select VIS and NIR bandwidths while eliminating infrared heat. The HIAPI also incorporated two optical trains, such that the light source was inserted (see FIG. 1) between the MTP and telecentric lens of the VIS CCD camera end for reflectance, and provided NIR light for transmission mode Chemical imaging on the opposite side. However, a single optical train for both cameras may require two light sources (reflectance; transmission mode) to provide for sequential image acquisition.

Filter Sets:

Greater quantitative accuracy for DMSO and water measurements used optical filters to produce two images: principally in the CH vibrational modes; and in the OH vibrational modes. This dual image analysis avoided covariance absorbance issues by separating the DMSO signal from that of water. Commercially available NIR interference filters are available in narrow and broad band-pass arrangements. These filters were implemented using a filter wheel either directly from the light source or within the camera body. Camera integration of the filters provided better NIR imaging but can introduce optical aberrations (image sharpness) and focal changes due to refractive index modification. Visible light filter sets can also be used to measure absorbance of light at defined bandpasses to aid in artifact detection or color determination.

Data Analysis and Software Tool Development:

it has been shown that a quantitative relationship for DMSO, water and volume content can be derived by simply using an unaided NIR camera image. However covariance (Δ water with Δ volume) was not addressed. This issue was resolved by separating the DMSO hand from the water band using a filter wheel. To resolve two overlapping spectra contributions a two point absorbance measurement was needed. NIR band-pass filters for signals at the 1.18µ and 1.55µ absorbance bands resolved DMSO and water respectively. Since two unknowns and two measurements are made, a Beer-Lambert derivation was applied to calculate the final concentrations [A=absorbance, e=molar absorptivity constant, b=pathlength and c=concentration].

$$A_{1.18\mu} = A_{water} + A_{DMSO} = e_{water}*b*C_{water} + e_{DMSO}*b*C_{DMSO}$$

$$A_{1.55\mu} = A_{water} + A_{DMSO} = e_{water}*b*C_{water} + e_{DMSO}*b*C_{DMSO}$$

Given the additional factor of pathlength, Simplex Optimization for an underdetermined system can be applied. Consequently two chemical images followed by image processing allow for well-volume and DMSO-hydration determination to be derived. The HIAPI system was validated from a number of MTP types (table 1). Since MTP well profiles vary vendor to vendor), non-linear relationships between well volume and depth was expected. Absorbance measurements with respect to quantitative DMSO and water analysis of nonlinear regressions dedicated for each plate type and manufacturer was conducted. For this work, a calibration set of DMSO samples with water varying from 0% to 30% was used for regression model training. Evaluation was performed using the same samples doped and undoped with 100 mM compound mixture (TBD) and placed randomly within various test plates. The analysis was deemed successful if reported quantities were within 10% of the actual value eliminating the need for a priori knowledge of the sample and allowing for post-processing damsel to be mining. Differential hyperspectral image analysis was used as QC test for compound plate fidelity.

Instrument Calibration and Evaluation:

The software process of analyzing a microtiter plate for artifacts was broken up into three major sections: image acquisition, image standardization and image analysis. After image acquisition and preprocessing steps were completed, the HIAPI analysis routine took the processed frames and inspected individual wells. The goal of this inspection was to classify each well by using characteristics available from the preprocessed image frame to determine compound/well problems (bubbles, ppt., empty, etc.). An initial prototyping of these classifications involved determining a set of static thresholds for a given microtiter plate. The calibrations may require validation from a number of MTP types (Table I).

| MTP Vendor/Type | | | Volume | | | Plate Defects & Artifact | | | % Water | Color |
|---|---|---|---|---|---|---|---|---|---|---|
| Vendor | Format | Material | Full* | Partial** | Empty* | Plate | Bubbles | ppt. | DMSO* | RBG |
| GREINER | 384-w | PP | NIR/VIS | NIR | NIR/VIS | NIR/VIS | NIR/VIS | NIR/VIS | NIR | VIS |
| GREINER | 1536-w | PP | NIR/VIS | NIR | NIR/VIS | NIR/VIS | NIR/VIS | NIR/VIS | NIR | VIS |
| COSTAR | 384-w | PP | NIR/VIS | NIR | NIR/VIS | NIR/VIS | NIR/VIS | NIR/VIS | NIR | VIS |
| COSTAR | 96-w | PP | NIR/VIS | NIR | NIR/VIS | NIR/VIS | NIR/VIS | NIR/VIS | NIR | VIS |
| NUNC | 384-w | PP | NIR/VIS | NIR | NIR/VIS | NIR/VIS | NIR/VIS | NIR/VIS | NIR | VIS |
| REMP | 384-w | PP | NIR/VIS | NIR | NIR/VIS | NIR/VIS | NIR/VIS | NIR/VIS | NIR | VIS |
| AURORA | 384-w | COC | NIR/VIS | NIR | NIR/VIS | NIR/VIS | NIR/VIS | NIR/VIS | NIR | VIS |

*Only determined as present or missing,
**NIR mode provides exact quantitative values.

and reproducibility of the measurement was within ~3% variance. Finally, actual compound plates will be evaluated to generate a plate map view of DMSO hydration. Results were compared to destructive sampling of select wells using refractive index measurements or an acoustic auditing appliance during the beta-testing phase.

When a NIR camera EPA was aligned with MTP well rows, signal transects across select pixel rows provided a wealth of information as discussed above. Normal wells with dissolved compound produced strong even plateau that illuminated the entire well, producing a wide-flat peak. Crystallization produced jagged peaks while air bubbles manifested as irregular shaped plateau, often clipped and narrow in width. First derivative analysis of pixel transected across well rows using minimal thresholds setting for height and width was developed for rapid and simplified QC determination of the compound well state. Large periodic inflection points mark solution/wall boundaries and were easily identified by first derivative calculations that triggered secondary inspection within the well domain for additional points of inflections. Given set threshold values, these secondary points of inflection signaled formatting problems such as crystallization or droplet formation.

Hyperspectral imaging is an advanced application development and part of a class of techniques commonly referred to as spectral imaging. With the application of heat-map image acquisition of optically filtered light a set of 'spectral images' was collected. Each image represented a range in the NIR spectral band. These 'images' were then combined and formed a three dimensional hyperspectral cube for processing and analysis. Hyperspectral documentation to generate plate libraries provided a means of comparing plate changes through time. The primary advantages to hyperspectral imaging is that multiple spectra is acquired at each pixel point, Success was measured by comparing software detection and tagging results of defect wells against the known pattern generated by a robotic liquid workstation or another appropriate method. Calibration and evaluation for sample precipitation can use a hydrophilic compound that can be forced out of solution by the addition of DMSO. For example, bicuculline methobromide was one such compound among many that had been identified to be problematic, in remaining soluble in DMSO. This method was validated by HPLC-MS to measure "compound as solute" prior and post precipitation. An alternative methodology can be borrowed from an accepted nephelometry protocol where an aliquot of silica suspension is dispensed with a liquid-handling workstation into a DMSO well to produce strong light scattering as a colloid.

Development of a Robust, User-Friendly Database Query Tool:

The HIAPI results database is important for documentation and review of HIAPI results within the user-interface software. The database itself functioned as a repository of experimental parameters and results for archival and documentation purposes. It was also useful for ad hoc queries to identify wells with particular features of interest. For example, queries to identify all "blue" wells returned a list of compound IDs, along with associated images and other features the user may be interested in. Queries were also conducted using SQL commands in a non-user-friendly interface; however, other embodiments address the construction of a user-friendly query tool that facilitated custom queries of the database. Creation of report templates by the HIAPI, user populated with selected HIAPI results, was also performed.

CCD Image Analysis; Precipitate and Artifacts:

CCD images of plates (MTP) were taken using visible light, and well analysis was executed for various defects and artifacts, as shown in FIG. 4. Presented are five well types including a full DMSO control well, partial filled well with bubble, colored compound, precipitated compound, and an empty well. Machine vision processing is emulated using MATLAB software and image analysis applications to convert the images to signals that can be translated by computers in real-time.

A six step process was used to reduce the initial image into an "object signature" (see last row of FIG. 4) with a digital threshold that is clearly distinct for each well type. In the first step, image subtraction front a completely empty MTP was performed. Normal wells (DMSO) and normal wells with colored compounds have binarized image objects which looked similar to toroids (i.e. donuts). The "object signature" for these was a flat plateau; the centroid of the object analyzed was very close to the absolute center of the image and its area is equivalent to the area of the well.

Calculation of an Euler number also aided in the analysis of these images; in this case it represented the number of objects detected in the image, minus the number of holes in the objects. Partially filled wells have "object signatures" which are erratic in shape and have significant variation in amplitude across the field. In terms of morphological properties, the centroid location can be offset from the center of the image and the object area can be noticeably less than the area of the well. Wells with precipitate are represented by a solid circular object in the binarized image and have flat signatures, similar to non-problematic wells. However the amplitude of the signatures was significantly lower than seen in the signature of a non-problematic well. These wells also had a different Euler number, an object area equivalent to half the area of the well and a centroid located in the center. Empty wells had a black image frame abler image subtraction from a control plate, so no further properties were necessary for classification. The "object signature" was zero across the field and quite different from the normal DMSO filled wells.

Image Processing:

Image processing began when all image data was imported to analyze MTP wells as selected "Areas of Interest" (AOI). As a first step the extraction of color information was performed, which is evaluated in terms of pixel intensity at each color channel. Clearly visible in the first row of "raw" CCD images (FIG. 4) was the presence of a red compound. The resulting, color channel histograms from this image were immediately used to determine the color(s) present in a well and any variance across, since it will combine later with other downstream determinations to better classify the well type present (e.g. "red"+"precipitate"="red precipitate"). Following the extraction of all color channel data, image subtraction was performed from an empty control plate. If a test well was empty, it resulted in a "black" image and there was no further processing necessary. If the well was not empty, then the resulting image highlighted the distinguishing features quantified in its 2-D matrix. Note that extraneous information, such as the data representing plastic around the well was not present in this image. The next step illustrated was the conversion of the subtracted image into grayscale (FIG. 4). This removed color information, which was not necessary for downstream processing. While this rendered the data matrices representing the image from 3-D to 2-D, the intensity values representing objects of interest were retained. When the image is at this stage, meaningful information can be obtained in the form of grayscale histograms and "distance" profiles. Grayscale histograms and distance profiles provided an assessment of pixel intensity across a selected cross-section of the well. In the case of MTP analysis, the selected cross-section passed horizontally through the center of the well. The last stage of image processing used a threshold to convert the grayscale image to a binary image. The end result represented the objects present in a given well that had an intensity greater than the defined threshold. These binary objects underwent enhancement routines to remove spurious objects which might otherwise be identified as false positives in downstream analyses. Finally, the enhanced binary objects was put through algorithms to extract and plot their boundaries, known as "object signatures". These results were successful in identifying the state of a MTP compound well and its artifacts. When optimized, the methodology lends itself quickly to frill automation.

Figure 5A:
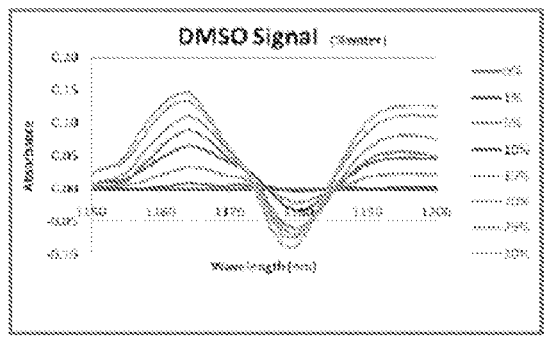
FIG. 5A is a graph showing an NIR spectral overlay of 70-100% DMSO samples.
Figure 5B:
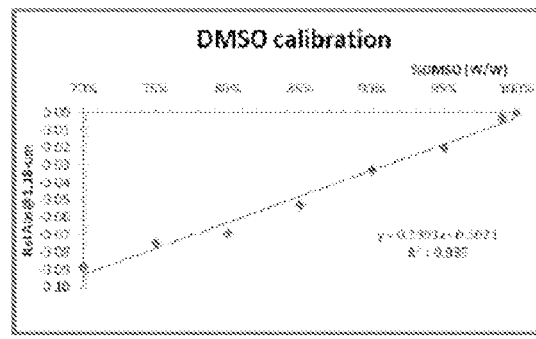
FIG. 5B is a graph showing, a quantitative DMSO analysis at 1.18 microns.
Figure 5C:
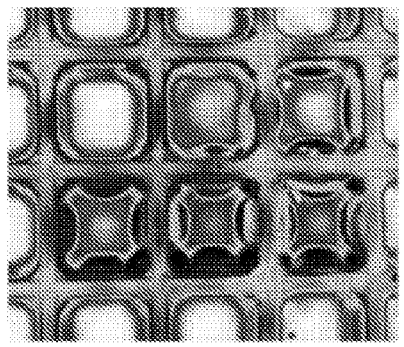
FIG. 5C is a scan of a photograph showing NIR imaging of DMSO (false colors) filled wells within a 384 polypropylene plate, at 0 µL, 20 µL, 40 µL, 60 µL, and 80 µL of volume.
Figure 5D:
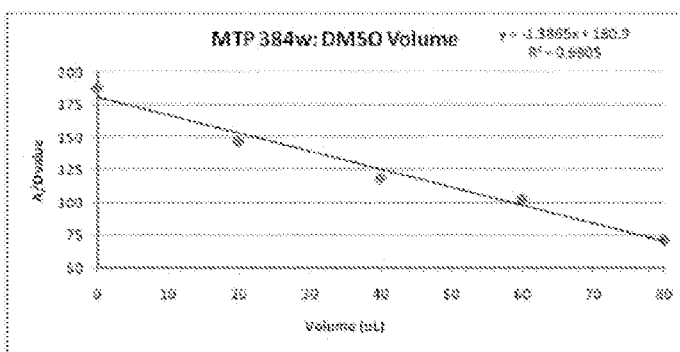
FIG. 5D shows a linear regression and fit to the well data using the central 6,400 pixels.
Figure 5E:
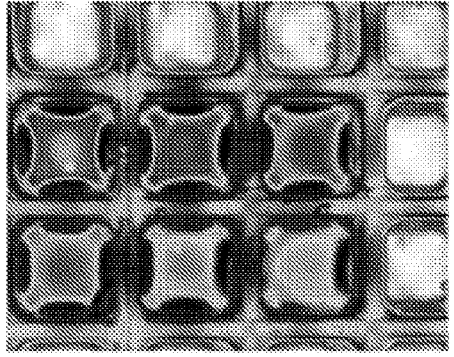
FIG. 5E is a scan of a photograph showing the NIR imaging of water in DMSO (false colors) using a 384 polypropylene plate (empty wells shown in orange). Six wells from top left to bottom right were tilled with 0%, 5%, 10%, 15%, 20% and 25% water (w/w) in DMSO.
Figure 5F:
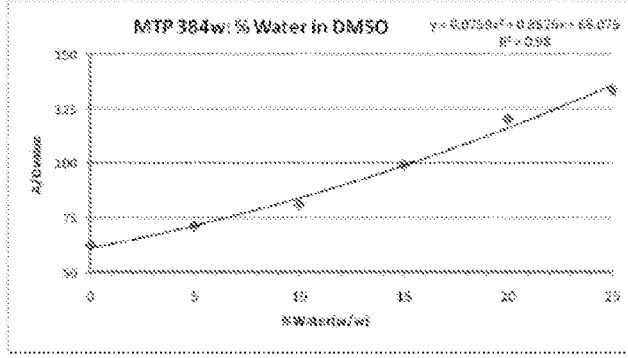
FIG. 5F shows a second order regression and fit to the AOI (6,400 central pixels) of each well.
Figure 5G:
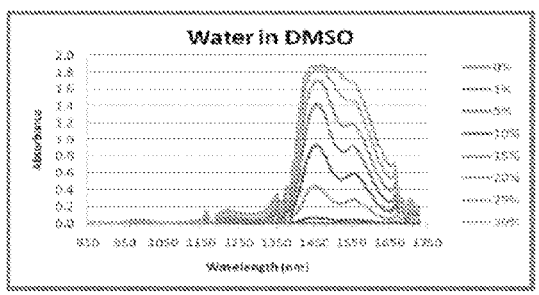
FIG. 5G shows a NIR spectral overlay of 0-30% Water/DMSO.

Near-Infrared (NIR) Analysis:

The NIR range at ~0.7-2.5 microns is at an intermediate region of the electromagnetic spectrum, between the imaging, capabilities of visible light and the chemical fingerprinting of infrared spectroscopy. The data presented both spectroscopic and imaging features that can be exploited for nondestructive analysis of HTS compound collections. Weak absorption arises from overtone and combination stretching/bending of the O—H and C—H bonds. These weak NIR interactions are an important asset, allowing for deep penetration into a sample for both qualitative and quantitative information. NIR analysis may well suited for water content analysis of dimethyl sulfoxide (DMSO), without interference from the solvated pharmaceutical compound. To demonstrate these features, DMSO and water samples were analyzed in the NIR region as presented. A calibration set of eight samples was prepared to span the 0-30% range for water in DMSO (v/v). Calibration samples were placed into 1-cm spectrometric cuvette and analyzed on an Ocean Optics NIRD121 spectrometer and data in FIG. 5G presents the raw NIR absorbance scans.

Figure 5H:
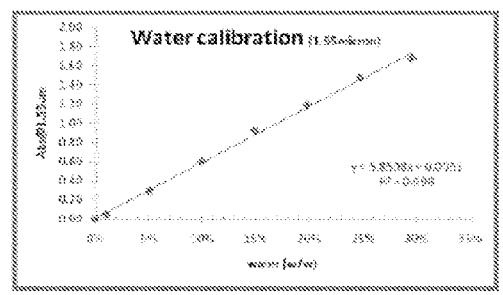
FIG. 5H shows quantitative water analysis by NIR at 1.55 microns.

Water vibrational bands at 1.45-1.55-μm were assigned to the first combination and the first overtone vibrational modes of the OH-bond. Although some overlap with CH-vibrational bands can occur, the 1.55-μm region was relatively free of any interference demonstrating excellent linearity with water content (FIG. 5H).

DMSO Analysis was also possible from several CH absorption bands, including the 1.69 and 1.71-μm doublet and the 1.18-μm singlet that can be assigned to first combination and first overtone vibrational modes. In particular, the 1.18-μm band was unique to CH vibrational, modes and relatively free of water interference as shown in FIG. 5A. A linear calibration can therefore be performed for DMSO with a diminishing series of absorbance peaks at 1.18-μm as shown in FIG. 5B.

Figure 5I:
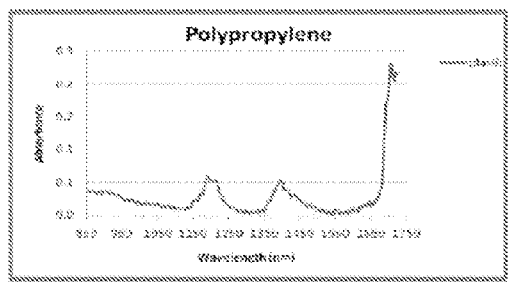
FIG. 5I is a plot showing NIR results from a polypropylene plate at 1.2 mm thickness.

MTP and NIR absorbance occurred as the plastic (typically polypropylene) contributed to the 1.69 and 1.71 μm, 1.18 μm singlet vibrational modes for CH stretch as shown in FIG. 5I. This absorbance contribution was a fixed constant that was corrected, by signal subtraction from a control plate from each plate type.

Figure 5J:
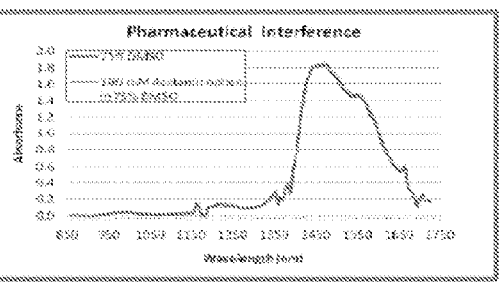
FIG. 5J is a plot showing NIR results from 100 mM acetaminophen in 75% DMSO and 75% DMSO alone.

Compound Interference is unlikely since their concentrations are no more than 100 milli-molar and are predicted to produce a CH vibrational absorbance >2 decades below that of DMSO. Consequently, quantifying water and DMSO in the NIR region was free of interference from solvated compounds. This is demonstrated in FIG. 5J where a sample of 100-mM acetaminophen in 75% DMSO (water balance) was compared against a DMSO control.

In summary, NIR spectroscopy was well suited for the QC analysis of compounds stored in plastic, consumables.

NIR Chemical Imaging (CI) Platform:

Recent developments in NIR imaging technology have led to the advancement of InGaAs focal plane arrays (EPA) with outstanding sensitivity in the 900-1700-µm range. A SC4000 SWIR FLIR camera with a 320×256 pixel array was selected for this work and has a high speed readout (420 Hz) without the need for any special cryogenic support. The camera was coupled to a 0.08× primary magnification telocentric lens. A quartz tungsten-halogen (QTH) lamp with a light diffuser was used as a blackbody NIR radiator. Optical analysis was performed in transmission mode.

Wafer and DMSO by NIR Chemical Imaging: NIR-imaging can be used for qualitative assessment with DMSO volume was tested using a 384-w polypropylene plate (Costar 3965) and filled with varying levels of respect to sample volume and levels of hydration. To demonstrate this capability, a 384 well MTP plate was selected and filled with varying levels DMSO and water. Image analysis of the central AOI (6,400 pixels) of each well provided the average profile intensity for each volume.

DMSO volume was tested using a 384-w polypropylene plate (Costar 3965) and filled with varying levels of pure DMSO. The absorbance gradient observed from the top left well to the bottom right is principally due to CH overtone/combinational vibrational mode absorbance. Note that the images produce a cross-like pattern (FIG. 5E) due to the additional CH overtone/combinational contributions from the polypropylene plate. DMSO spatial analysis of the central 6400 pixels for each well provides an average volumetric profile intensity that has a linear relationship to depth.

The same analysis was applied for qualitative assessment of compound plates with respect to water content. As shown in FIG. 5F, the same 384-w polypropylene plate (Costar 3965) was selected and filled to a set volume of 50-µL for all wells tested. Several mixtures of water to DMSO (Top left to bottom right: 0%, 5%, 10%, 15%, 20%, 25%) were tested. Using the protocol described above, the profile intensity of each well was determined and the data was fined to a second order curve (FIG. 5F). Unlike the NIR spectrophotometer, a linear relationship was not found due to the additional contribution of CH vibrational modes from the DMSO. Future work can use optical filters on the NIR camera to separate bandwidths for OH and CH vibrational modes. Nevertheless, the unaltered NIR camera tested demonstrates "proof-of-concept" with respect to Chemical Imaging and quantitative analysis that can be extrapolated from NIR images.

Figure 6A:
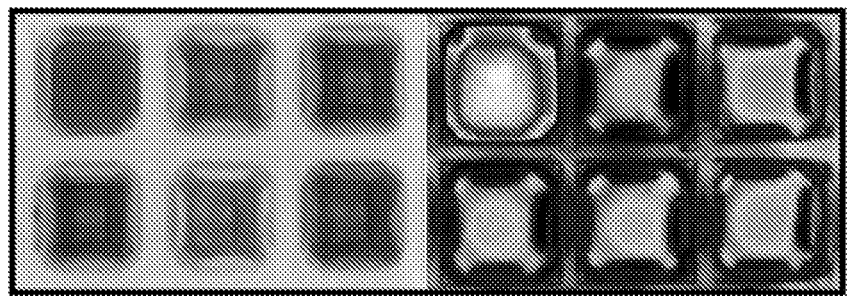
FIG. 6A is a scan of a photograph showing: Top-six wells were imaged using visible light (left) and NIR light (right). The wells contents are (top left) 1) Empty; 2) 100-mM Yellow-#5 dye; 3) 100-mM Blue-#1 dye; 4) Green dye (blue-yellow combined); 5) DMSO; 6)~100-mM red-#40 dye.
Figure 6B:
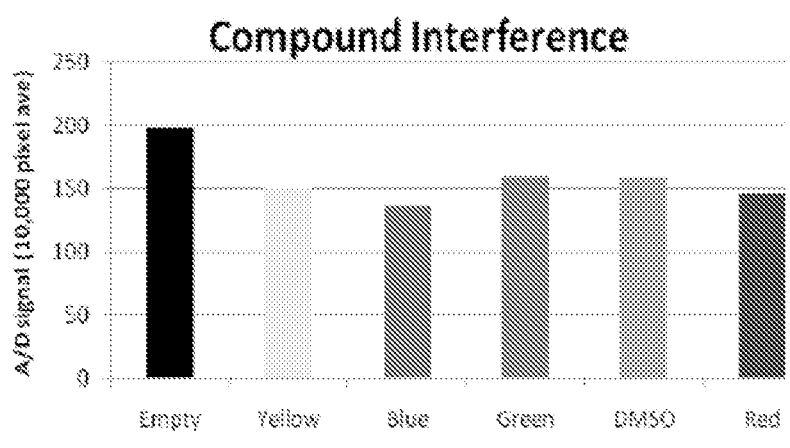
FIG. 6B is a bar graph plot of the average pixel value (1,000 pixel average) confirming the lack of any color distinction by NIR.

Compound Interferences and NIR Chemical Imaging:

Solvated pharmaceuticals in DMSO are generally less than 100 millimolar and were predicted to produce a CH vibrational absorbance >2 decades below that of DMSO. FIG. 6A presents two 6-well images juxtaposed to present a "visible light" image and a "NIR" image of the identical MTP wells. From upper left to lower right corners the test wells were filled using color dyes as described (FIG. 6A). Although the images were vividly distinct in the visible light CCD imaging, they were unremarkable by NIR imaging. A bar graph plot (FIG. 6B) of the average pixel value (1,000 pixel average) also confirmed the lack of any color distinction. The lack of significant absorbance also applies to colorless compounds.

Figure 7:
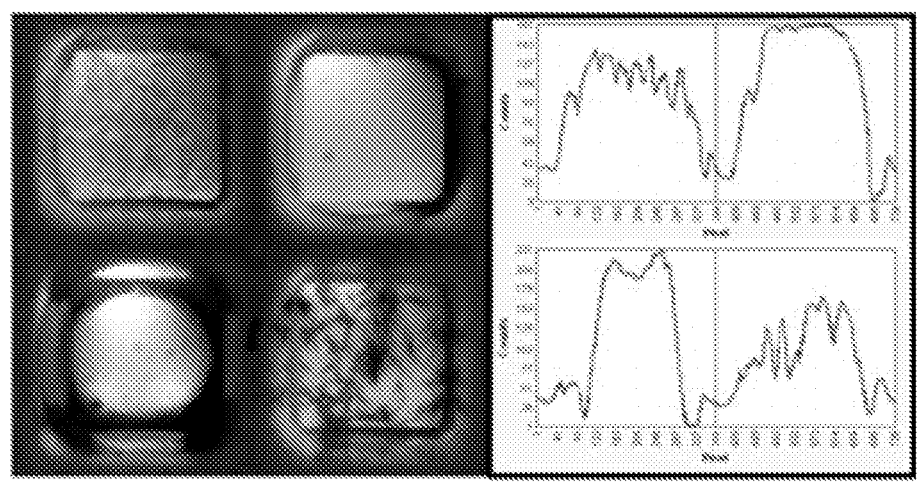
FIG. 7, left panel, is a scan of a photograph showing NIR images (displayed from upper left to lower right) of precipitate; dissolved compound ("normal"); a large air bubble and crystallization in different wells of NUNC 384 well polypropylene plate. Left panel shows a pixel profile which transects across each corresponding well of the plate depicting how the signal intensity and shape varies with each phenomena.

The HIAPI enhances the visibility compound precipitate, crystals and bubbles. FIG. 7 is a NIR image of four wells with these different artifacts present. Noteworthy is that the dissolved compound produced no absorbance; however concentrated compounds (i.e. crystals) exhibited a strong NIR absorbance (CH combinational/overtone modes). The pixel signal transect of the four imaged wells clearly indicated profiles unique to each artifact deviations. The "normal well" with dissolved compound produced a strong, even plateau that illuminated the full well, corresponding to a wide-flat peak. Crystallization produced several jagged peaks while air bubbles manifested as irregular shaped plateau, clipped and narrow in width. First derivative analysis of pixel transects across well rows with minimal thresholds for height and width was developed for rapid QC determination of these different compound states.

Figure 8:
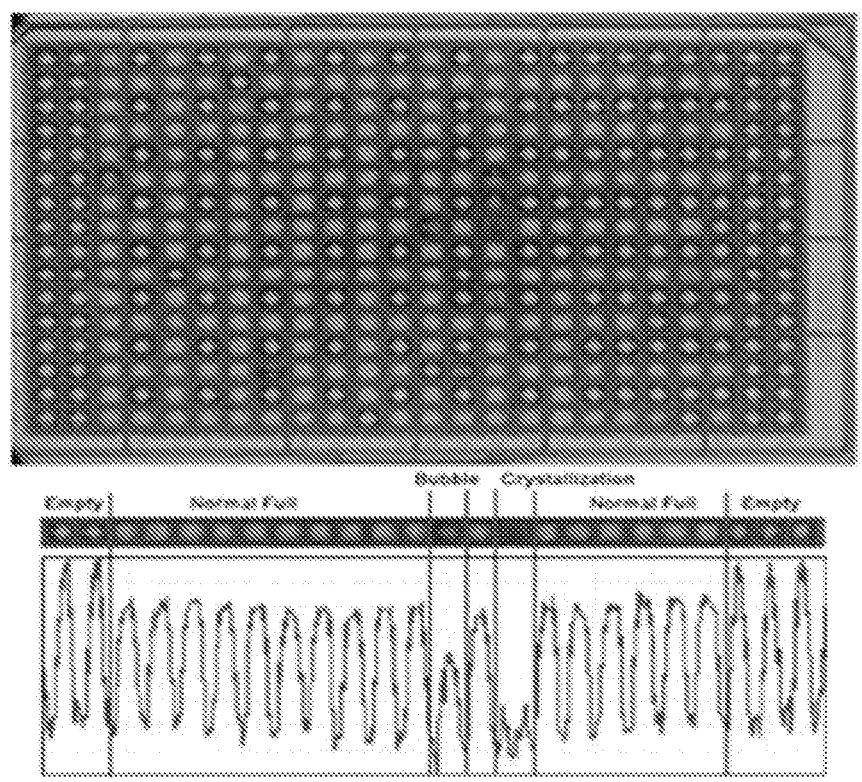
FIG. 8, top panel, is a scan of a NIR image showing a NUNC 384 polypropylene compound plate imaged by the NIR-HIAPI system. The bottom panel shows row "1" of the plate which contains different artifacts in each well and these artifacts are correlated to a pixel profile transect. The empty wells have higher narrow peaks than full wells (height/width variance), while defects such as crystallization show up as a jagged profile. Bubbles typically manifest as an irregular profile with a sharp signal drop along one or both edges of a well.

Despite its lower resolution, the NIR camera's 320×256 pixel array can be used for full-plate analysis. Shown in FIG. 8 is the NIR image from a NUNC 384 compound plate (Cat#264573) with several artifacts. When imaged in the NIR-HIAPI (top-view imaging), various artifacts are clearly visible. Simple pixel transect profiling distinguishes wells containing artifact: specifically, the pixel transect of row "I" and demonstrates a simple "visual to digital" conversion of information.

Figure 9:
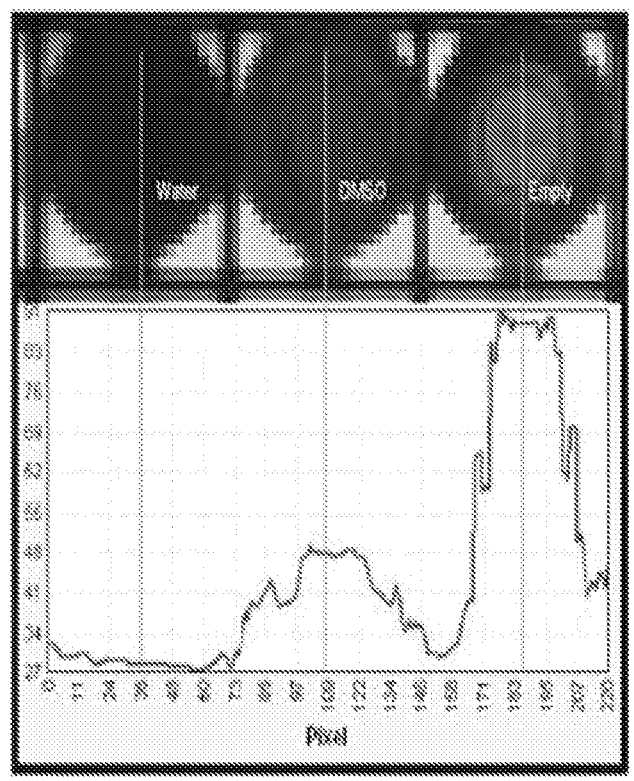
FIG. 9 shows 1.4 mL, screw-top tubes imaged using the NIR-HIAPI system over a 52 mm pathlength, DMSO filled, water filled and empty tubes are distinct visually and by pixel profile transect.

The ability of NIR to penetrate deeply into a sample can be used to analyze microtubes, another type of popular consumable used for storage of HTS compound libraries (FIG. 9). For this experiment, three tubes were assembled and sealed prior to imaging. As shown in FIG. 9, from right to left these tubes are 100% water; 100% DMSO and empty.

NIR imaging was performed across a variety of tube and plate types as manufactured by different vendors. NIR images were performed in NIR transmission mode in "top-down" and "bottom-up" viewpoints. Four rows of samples were prepared to evaluate HIAPI capabilities with respect to compound interference; well volume; precipitation detection and solvent composition (Water/DMSO). The results are detailed in Table 1, above.

MTP Plate Automation HIAPI Instrument:

The HIAPI can be automated, for example, with respect to plate handling. A number of commercial products are amenable to a plate storage and retrieval system, with hardware to pick plates from the storage device (e.g. a plate carousel) and place them on the HIAPI stage for analysis, then return the plate to the storage device after analysis has finished.

Advance Calorimetric Analysis Tools:

Color determination can aid HTS assay screening better when translated to wavelength transmission for spectroscopic interference determination. Two post-image analysis procedures comprise an algorithm that takes raw, unprocessed data from the camera's pixel sensors and processes it with knowledge of the Bayer filter spectral profile. The Bayer color filter array is a popular format for digital VIS CCD based acquisition of color images. Correlating RGB A/D signal values relative to the spectral functions would provide a direct way of estimating wavelength from color. An alternative approach would be to take a processed frame and extract color information by examining color space (RGB, HIS, CIE) data. A user could define boundaries representing colors or wavelengths of interest as These boundaries would then be used to partition color assignments into wavelength domains.

Advance Image Analysis Tools:

In addition to specific techniques discussed, the overall usefulness and usability of the instrument was increased by applying machine learning techniques. The QA measurements were based on pre-determined thresholds set for each MTP type and tuned with calibration standards. However, advanced versions of HIAPI analyses can allow the user to interactively classify individual wells within a microtiter plate through a GUI interface. The data gathered during this pre-inspection classification can then be processed using machine learning algorithms to allow quick training of unique artifacts, generating better accuracy and allowing for the addition of alternative labware. These same machine learning algorithms can provide a post-inspection QC option, which provides an operator a means to verify QA measurements and make any necessary corrections within the same interactive GUI. Corrections would then be added to a training knowledge base and used to increase the overall accuracy of the instrument. By extending the classification to include machine learning algorithms, the HIAPI platform can also provide support for novel uses (e.g. micro-arrays, tubes) and detect previously undefined artifacts. An example of a new/undefined artifact may include analysis of MTP mold deformities (e.g. imbedded defects, stress fractures, broken plates), or extended use to HTS bio-assay plates for QC validation.

MTP Remediation Technologies:

Micro-scale remediation will examine the integration of drying agents with liquid handler workstations to provide selective water removal and recovery of precipitated compounds in MTP plates. Current methods using ultra-sonication to re-dissolve precipitated compounds generally fail, since increased. DMSO hydration is often the primary cause of decease solubility. Only the removal of water can remediate the problem. The Table below provides an illustrative example of potential drying agents.

TABLE 3

| Drying Agents | Suitable for Drying | g $H_2O$/g Desiccant | Regeneration | Reaction Mechanism |
|---|---|---|---|---|
| Aluminum Oxide | Hydrocarbons, air, ammonia, arogn, helium nitrogen, oxygen, Freon, $H_2O$, $CO_2$, $SO_2$ | 0.2 | 175° C. | Chemisorption Adsorption |
| Cupric Sulfate | Esters, alcohols, benzene and toluene | 0.6 | 200° C. | Hydration |
| DRIERITE, Regular | Air, gases, organic liquids and solids. | 0.066 | 210° C. | Hydration |
| Molecular Sieve Type 3A $K12[(AlO2)12(SiO2)12]\cdot X\ H2O$ | Molecules of diameter > 3 Å: Considered a general-purpose drying agent in polar and nonpolar media | 0.18 | 117-260° C. | Adsorption |
| Molecular Sieve Type 4A $Na12[(AlO2)12(SiO2)12\cdot X\ H2O$ | Molecules of diameter > 4Å: Generally considered a universal drying agent in polar and nonpolar media | 0.18 | 250° C. | Adsorption |
| Molecular Sieve Type 13X $Na86[(AlO2)86(SiO2)106]\cdot X\ H2O$ | Molecules of > 10A: used for drying hydrocarbons | 0.25 | 200-315° C. | Adsorption |
| Silca Gel $Na2SiO3\cdot xH2O$ | Most organics | 0.2 | 200-350° C. | Adsorption |
| Zinc Chloride | Hydrocarbons | 0.2 | 110° C. | Hydration |

In particular, Zeolites are molecular sieves (3A & 4A) that are highly-selective for water and have been used to dry DMSO to 10-ppm46 or less. It is estimated that only ~15-mg of a 4A sieve is needed to dry a 10-μL sample of ~30% water in DMSO from a 1536 compound plate. Zeolites are available as powders (~5-10 micron) or as extruded, pellets/spheres. Spheres of 14-30 mesh site are commercially available with a 0.6-1.4 mm diameter. Such spheres can be easily packed into disposable micro-pipette tips, without significant flow interference, and used with a liquid handler workstation to automate the liquid withdrawn. Drying agents can also be obtained with a visible indicator for moisture using ammonium tetrachlorocobaltate(II) $(NH_4)_2CoCl_4$ or cobalt chloride $CoCl_2$. This will cause the agent to be blue when dry and pink when hydrated for visual verification. Several drying agents (table 3) are selected for testing on disposable tips for 384-w and 1536-w plates. Water removal from DMSO can be tested using either NIR analysis or through refractive index measurements, leading to direct testing of precipitated compounds in MTP wells. To drive solubility to completeness, each treated plate can be resealed and heated using a plate sonicator. Plates can be visually inspected after 24-hrs post treatment for precipitation and can be used to QA the molecular mass and quantity.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the Disclosure is provided to allow the reader to quickly ascertain the nature of the technical disclosure. It is submitted with the understanding that it will not be used to interpret or limit the scope or meaning of the following claims.

What is claimed:

1. A system comprising:
a full-spectrum, ultraviolet, visible, infrared or near infra red light source for irradiating a consumable or consumable comprising a sample;
at least one lens in optical alignment with light reflected, transmitted through or emitted from the sample, wherein the at least one lens comprises a telecentric lens in combination with a high-resolution progressive scan charge-coupled device (CCD);
at least one sensor for detecting reflected light from the sample or light transmitted through the sample;
a computer or processor running software for processing and analyzing the reflected or transmitted light.

2. The system of claim 1, further comprising at least one filter in optical alignment with the light source or sensor for receiving light emitted from the light source.

3. The system of claim 2, wherein a filter comprising at least one of: AOTF, liquid crystal, polarized, attenuated, dichroic, emission, excitation, longpass, shortpass, bandpass, notch coated, dielectric, Bayer filter, or light diffuser.

4. The system of claim 1, wherein the light source, comprising: blackbody radiator, IR, UV, visible, laser, monochromatic, polychromatic, LED, tungsten-halogen, quartz-tungsten halogen, Hg arc lamp, Xe arc lamp, electroluminescence or combinations thereof.

5. The system of claim 1, wherein the at least one sensor is in optical alignment with at least one lens for focusing light reflected or emitted from or transmitted through the consumable or consumable comprising a sample.

6. The system of claim 1, wherein the at least one sensor comprising: CCD, Photodiode, Photo multiplier tube, IR-NIR arrays, Focal Plane Array, InGaAs photodetector; Vis-GaAs photodetector, InSb photodetector, Quantum Well Infrared photodetector or combinations thereof.

7. The system of claim 1, wherein the sensor is an image sensor and captures an image of the reflected, emitted or transmitted light from the sample, consumable or consumable comprising a sample.

8. The system of claim 7, wherein the captured images are standardized prior to analysis by the software.

9. The system of claim 7, wherein standardization of images by the software comprises at least one step of:
    selecting an area of interest for analysis;
    compensating for environmental artifacts;
    comparing each pixel value to an assigned threshold value;
    identifying and enhancing objects;
    segmenting the image.

10. The system of claim 7, wherein the standardized image is analyzed and results stored.

11. The system of claim 1, further comprising a graphical user interface and one or more databases.

12. The system of claim 1, wherein said sensor comprising a charge-coupled device (CCD), focal plane array (FPA), near-infra red (NIR) sensor, NIR-VIS camera or combinations thereof.

13. A method of detecting and analyzing artifacts in a sample, consumable or consumable comprising a sample, said method comprising:
    irradiating the sample with ultraviolet, visible, infra red or near infra red light;
    capturing an image of light reflected from the sample or emitted or transmitted through the sample;
    processing and analyzing the image; and,
    detecting and analyzing artifacts in a sample, consumable or consumable containing a sample.

14. The method of claim 13, wherein the software standardizes the image prior to analysis, said standardizing comprising at least one step of:
    selecting an area of interest for analysis;
    compensating for environmental artifacts;
    comparing each pixel value to an assigned threshold value;
    identifying and enhancing objects;
    segmenting the image.

15. The method of claim 13, wherein analyzing comprises measuring at least one of: (a) volume of a liquid sample in wells (or microtubes) containing liquid sample, (b) detecting precipitate, objects or artifacts within microtiter plate wells, (c) classifying colored samples in microtiter plate wells or microtubes; (d) determining contaminants; (e) air bubbles; (g) problems with a consumable.

16. The method of claim 15, wherein DMSO and water are quantitatively assessed wherein
$A_x = A_{water} + A_{DMSO} = e_{water}*b*C_{water} + e_{DMSO}*b*C_{DMSO}$ and $A_y = A_{water} + A_{DMSO} = e_{water}*b*C_{water} = e_{DMSO}*b*C_{DMSO}$ where concentrations [A=absorbance, e=molar absorptivity constant, b=path-length and c=concentration].

17. The method of claim 16, wherein x is >0 and y is >0.

18. The method of claim 15, wherein the system further comprises robotic integration, automation, semi automation or combinations thereof.

19. The method of claim 15, wherein remediation of a contaminant comprises contacting a sample with a composition which selectively removes the contaminant.

* * * * *